US006203755B1

(12) United States Patent
Odland

(10) Patent No.: US 6,203,755 B1
(45) Date of Patent: *Mar. 20, 2001

(54) ELECTRON BEAM STERILIZATION OF BIOLOGICAL TISSUES

(75) Inventor: Thomas L. Odland, Lino Lakes, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/205,781

(22) Filed: Mar. 4, 1994

(51) Int. Cl.[7] .................................................. A61L 2/08
(52) U.S. Cl. ............................ 422/22; 422/23; 422/36; 435/1.1; 623/2
(58) Field of Search .......................... 422/22, 23, 28, 422/36; 435/1; 250/455.11; 623/2

(56) References Cited

U.S. PATENT DOCUMENTS

| | | | |
|---|---|---|---|
| 2,785,313 | * 3/1957 | Trump | 250/455.11 X |
| 3,451,394 | 6/1969 | Bechtol et al. | |
| 3,779,706 | * 12/1973 | Nablo | 422/22 |
| 3,808,113 | 4/1974 | Okamura et al. | 623/66 |
| 3,948,601 | 4/1976 | Fraser et al. | 422/22 |
| 4,120,649 | 10/1978 | Schechter | 623/1 |
| 4,264,155 | 4/1981 | Miyata | 351/160 H |
| 4,378,224 | 3/1983 | Nimni et al. | 8/94.11 |
| 4,456,589 | 6/1984 | Holman et al. | 424/95 |
| 4,466,139 | 8/1984 | Ketharanathan | 3/1.4 |
| 4,553,974 | 11/1985 | Dewanjee | 8/94.11 |
| 4,582,640 | 4/1986 | Smestad et al. | 260/123.7 |
| 4,620,908 | * 11/1986 | Van Duzer | 422/22 X |
| 4,647,283 | 3/1987 | Carpentier et al. | 623/11 |
| 4,671,797 | 6/1987 | Vrandecic Pedero | 623/1 |
| 4,681,588 | 7/1987 | Ketharanathan | 623/11 |
| 4,714,595 | * 12/1987 | Anthony et al. | 422/294 |
| 4,798,611 | 1/1989 | Freeman, Jr. | 8/94.11 |
| 4,800,603 | 1/1989 | Jaffe | 8/94.11 |
| 4,837,024 | 6/1989 | Michaeli | 424/446 |
| 5,043,426 | 8/1991 | Goldstein | 514/21 X |
| 5,096,553 | 3/1992 | Ross et al. | 204/157.15 |
| 5,141,747 | 8/1992 | Scholz | 424/424 |
| 5,989,498 | * 11/1999 | Odland | 422/22 |

FOREIGN PATENT DOCUMENTS 4-288165 * 10/1992 (JP) ............................. 435/1

OTHER PUBLICATIONS

Wedster's Ninth New Collegiate Dictionary, Merriam–Webster Inc. 1983, defintion of "tissue" p. 1237.*
"An Experimental Study on Processed Peripheral Nerve Grafting" by, A. Inoue, Kyoto Prefect Univ. Med., vol. 90 (4), 1981, pp. 323–337. (English Translation also submitted herewith).

"An Evaluation of Aortic Valve Homografts Sterilized by Electron Beam Energy" by, Malm et al., Journ. of Thoracic and Cardiovascular Surgery, vol. 54, No. 4, Oct. 1967, pp. 471–477.
Barnard et al., "Startup of the Whiteshell Irradiation Facility", *Nuclear Instruments and Methods in Physics Research*, 1–4 (1989).
Barnard, "E–Beam Processing in the Medical Device Industry", *Medical Device Tech.*, 2(5), 34–41 (Jul. 1991).
Bowes et al., "Crosslinking of Collagen", *J. Appl. Chem.*, 15, 296–304 (Jul. 1965).
Bowes et al., "The Reaction of Glutaraldehyde with Proteins and Other Biological Materials", *Journal of the Royal Microscopical Society*, 85(2), 193–200 (Apr. 1966).
Cheung et al., "Mechanism of Crosslinking of Proteins by Glutaraldehyde II. Reaction with Monomeric and Polymeric Collagen", *Connective Tissue Research*, 10(2), 201–16 (May 1982).
Cheung et al., "The Effect of γ–irradiation of Collagen Molecules, Isolated α–Chains, and Crosslinked Native Fibers", *J. Biomedical Materials Research*, 24, 581–589 (1990).
Dahm, et al., "Immunogenicity of Glutaraldehyde–Tanned Bovine Pericardium", *J. Thorac. Cardiovasc. Surg.*, 99, 1082–90 (1990).
Gendler et al., "Toxic Reactions Evoked by Glutaraldehyde–Fixed Pericardium and Cardiac Valve Tissue Bioprosthesis", *J. Biomedical Materials Research*, 18, 727–736 (1984).
Grimm et al., "Glutaraldehyde Affects Biocompatibility of Bioprosthetic Heart Valves", *Surgery*, 111, 74–78 (1992).
Jacobs et al., "The Reconstruction of Powders for Injection with γ–irradiated Water", *International Journal of Applied Radiation & Isotopes*, 32, 180–181 (1981).
"Power Coatings to Recycling: Radiation Curing", *Kirk–Othmer Encyclopedia of Chemical Technology*, 3rd ed., 19 (N.Y.: John Wiley & Sons), 607–624 (1982).
Margel, "Characterization and Chemistry of Polyaldehyde Microspheres", *Journal of Polymer Science: Polymer Chemistry Edition*, 22, 3521–3533 (1984).
Rangwalla et al., "Electron–beam Sterilization and its Application to Aseptic Packaging", *Pharmaceutical Technology*, 36–47 (Nov. 1985).
Saunders et al., "Radiation Effects on Microorganisms and Polymers for Medical Products", *Medical Device and Diagnostic Industry*, 88–92 & 222 (May 1993).
Weadock et al., "Evaluation of Collagen Crosslinking Techniques", *Biomat., Med. Dev., Art. Org.*, 11(4), 293–318 (1983–84).
Woodruff et al., "Use of Glutaraldehyde and Formaldehyde to Process Tissue Heart Valves", (Shiley Scientific, Inc., 1978).

* cited by examiner

Primary Examiner—Krisanne Thornton
(74) Attorney, Agent, or Firm—Westman, Champlin & Kelly; Peter S. Dardi

(57) ABSTRACT

The invention involves a method for sterilizing biological tissues. The invention also includes sterilized biological tissues.

19 Claims, 6 Drawing Sheets

ELECTRON BEAM STERILIZATION OF BIOLOGICAL TISSUES

TECHNICAL FIELD

The invention involves sterilized biological tissues and methods for sterilizing biological tissues.

BACKGROUND OF THE INVENTION

Surgical implantation of tissue is utilized to replace and/or repair human tissues. For example, hereditary defects, disease, and/or trauma may damage tissues such that replacement and/or repair is desirable. These implantable tissues may be provided by individual human donors. However, because of the scarcity of appropriate human donors, non-human tissues have been increasingly employed instead. Such biological tissues have been used to replace heart valves, ligaments, tendons and skin, among other tissues.

Biological tissues derived from non-human or non-self sources may pose formidable problems to the new recipient. For example, the recipient's immune system may react to the implanted tissue and form an immune response, potentially leading to rejection of the implanted tissue. Thus, the new tissue may become ineffective and/or exhibit poor durability once implanted.

Conventionally, glutaraldehyde has been used to address some of these problems and to stabilize the tissue against in vivo enzymatic degradation. Additionally, glutaraldehyde has been used as a sterilizing agent to inhibit the infectivity of implant tissue. Glutaraldehyde cross-links proteins rapidly and effectively, particularly proteins such as collagen. This treatment increases resistance to proteolytic cleavage and hence increases resistance to enzymatic degradation.

In addition to crosslinking with glutaraldehyde, it is also well known to sterilize the crosslinked tissue with gamma radiation and the like prior to storage of the biological tissue.

Gamma radiation, and similar sterilization protocols, transfers energy to material primarily by Compton scattering i.e., scattering involving elastic collisions between incident photons and unbound (or weakly bound) electrons in which the incident energy is shared between the scattered electron and the deflected photon. These electrons recoil a short distance as unbound electrons, giving up energy to the molecular structure of the material as they collide with other electrons, causing ionization and free-radical formation. The scattered gamma ray carries the balance of the energy as it moves off through the material, possibly to interact again with another atomic electron. Since the probability for Compton scattering is low, gamma rays typically penetrate relatively deeply into the tissue before scattering occurs. Accordingly, gamma rays deposit energy in material over relatively large volumes so that penetration is typically high (typically greater than 50 cm in unit-density material) but dose rates are typically low (typically about a maximum of 20 kGy/hr). See FIG. 1.

Most techniques for sterilizing biological tissues produce undesirable results in the material, but the undesirable results may be more prominent when gamma radiation is used. Such undesirable results include but are not limited to the formation of radicals, hydrogen, and low-molecular-weight hydrocarbons; increased unsaturation; discoloration; and oxidation. Furthermore, gamma radiation typically requires a low dose rate in combination with a high exposure period, and degrades the structure of most conventional packaging materials.

Biological tissues prepared by the prior art methods suffer from a number of disadvantages, which limits their use in implantation, particularly human implantation. First, the use of some chemical sterilizing agents e.g., glutaraldehyde, increases the risk that a toxic response will be evoked in sensitive individuals, even after thorough rinsing of the tissue prior to implantation. Second, the use of certain sterilizing agents requires that the tissue be sterilized prior to packaging, thus necessitating a packaging step which must be carried out under stringent aseptic conditions. Third, gamma radiation can degrade polymeric materials employed in packaging by facilitating damaging oxidative reactions of polymers. Fourth, because gamma radiation typically involves relatively low dose rates, correspondingly long periods of exposure to effect sterilization may be necessary.

Thus there is an unaddressed need in the art for a method of sterilizing biological tissues that minimizes the possibility of immune rejection. Additionally, there exists a long-felt need for a method of sterilizing that does not necessitate an aseptic packaging step. Further, there is a need in the art for a method of sterilizing tissues which does not degrade the polymeric materials employed in packaging sterilized biological tissues. There is also a need for a method of sterilizing biological tissues that is quick, efficient, and results in a biological tissue with enhanced performance characteristics.

SUMMARY OF THE INVENTION

The present invention encompasses sterilized biological tissues and methods of sterilizing biological tissues which reduce or eliminate the disadvantages noted above.

In accordance with the present invention, biological tissues are treated by exposing the tissue to E-beam radiation sufficient to effect sterilization. Additionally, the present invention provides a biological tissue sterilized by E-beam radiation, with the resulting biological tissue exhibiting enhanced performance characteristics. The methods and tissues according to the present invention have the added advantage of reduced risk of infectivity, and eliminates the need for aseptic handling protocols. Further, the methods and tissues of the present invention, which use fewer reagents and/or require less processing, provide for lower costs in labor, reagents, time and personnel. E-beam radiation sterilization is effective in obviating the need for toxic sterilizing chemicals. Moreover, the amount of radiation required for E-beam sterilization does not significantly degrade the biological tissue, thus providing a more durable transplantable tissue.

There are a large number of characteristics that distinguish accelerated electrons from gamma rays:

Source of Radiation. Gamma rays are emitted by the decay of Cobalt-60. E-beams are produced by accelerating electron systems such as linear accelerators, Dynamitrons, and Van de Graaff generators.

Dose Rate. The dose rate for gamma radiation is approximately 110 grays per minute and the dose rate of E-beam is approximately 7800 grays per minute. Consequently, exposure times are dramatically greater for gamma radiation, which requires low doses over an extended period to effect sterilization. In contradistinction to gamma radiation, the high dose rates involved in E-beam irradiation promote diffusion of oxygen into biological tissue at a rate insufficient to participate in free radical formation reactions, such as those which might contribute to tissue and polymer degradation. This is particularly advantageous in those embodiments which include placing the biological tissue in a container prior to irradiation, since polymer degradation in both the tissue and the container may be minimized.

Furthermore, the high dose rate of E-beams relative to gamma rays permits a higher processing rate of sterilization, commonly an order of magnitude higher. For example, the sterilization period may be a matter of minutes for E-beam treatment, in contrast to the hours or more for gamma radiation treatment. Yet despite the higher dose rate, the present process does not result in significant degradation of biological tissue during the sterilization process.

Penetration. In relative terms, gamma radiation penetrates approximately ten times further into materials than 10 MeV electrons in the same material. Because the probability for electron-electron and electron-nuclear scattering may be high (relative to Compton scattering), 10 MeV E-beams typically penetrate approximately 5 cm in unit-density material before losing their energy. Thus, the power in the beam is typically deposited within a narrow range in the material and concentrated within the width of the beam. This results in high dose rate and low penetration (300 kGy per pulse, with an average dose rate of $2.2 \times 10^4$ kGy/hr for a 50 kW beam; 5 cm depth).

Directionality. The material is bombarded with electrons from a single direction, whereas materials are exposed to gamma rays from all directions.

Uniformity of Exposure. A more uniform reaction is achieved from gamma radiation than from E-beam radiation. Limited and differential penetration through materials result in "shadowing" with E-beam.

Source of Excited Electrons. Gamma rays induce excitation of electrons within the atoms of the materials to be sterilized. Electron beams, on the other hand, provide high-energy electrons to the exterior of the material, which in turn put subsequent electrons in motion.

Polymer Dose Response. Several studies report differences in the response of polymers, particularly polyethylene and polypropylene, to gamma and E-beam radiation. Because of the relatively high dose rate of the E-beams, oxygen is not capable of diffusing into the material at a rate required to participate in oxidative reactions that may lead to degradation of the material.

Furthermore, prevention of degradation in both the package and the tissue permit terminal sterilization, i.e., sterilization of the tissue in its final, sealed package. Thus, the present invention avoids the need for costly aseptic handling techniques, and provides sterility assurance as long as the package is intact, i.e., until the tissue is ready for use.

Micro-organism Dose Response. Early studies by an independent agency suggest a difference in the response of certain bacteria to gamma and E-beam radiation.

Dose Build-up. The phenomenon called build-up occurs with electron beam radiation only. As high energy electrons penetrate the surface they collide with atomic electrons of the material. These electrons, in turn, recoil and collide to set more electrons in motion so that from a relatively few electrons penetrating the surface, there results a multiplicity of electrons depositing energy in the material, primarily by the production of ions and free radicals. This process, called buildup, results in higher doses being delivered to depths below the surface where the primary beam and its recoil electrons can no longer produce ionization. Thereafter, the electrons quickly lose their remaining energy, primarily by soft interactions with atomic electrons (excitation) and radiative losses.

Precise and Reliable Dosimetry. E-beam dose can be carefully controlled because each product is irradiated individually on a conveyor, a factor which may be very important when critical doses are required. On the other hand, in a gamma facility many packages of a wide variety of materials are irradiated simultaneously. The dose delivered to each package may subsequently vary due to shielding effects caused by the density differences among the products.

Option of Differential Irradiation. With E-beam radiation, each package is irradiated individually with its own specified beam current, energy and exposure time. Additionally, parts of a package may be irradiated at a different level than other parts of the same package. For example, with E-beam radiation it is possible to irradiate half of a box with a dose of 10 kGy and the other half of the box with 25 kGy. It is also possible, using the limited penetration of E-beam to one's advantage, to shield sensitive parts of an object.

Ease and Safety of Operation. With the levels of energy utilized in an E-beam facility, there is little or no activation (induced radioactivity) of materials. Therefore, when the accelerator is turned off there is no danger of radiation hazard. Furthermore, there are no specific requirements for handling, monitoring, or disposing a radiation source. Temperature Rise. An issue that must be carefully considered when using ionization radiation to sterilize collagen-based materials is that of heat generation during the irradiation process. The temperature rise per megarad (Mrad) of deposited energy (1 Mrad=10 kGy) is calculated by dividing the heat equivalent of a, Mrad (2.39 calories/gram) by the specific heat of the material. This formula applies to both E-beam and gamma radiation. For biological vascular graft tissue and packaging solutions (specific heat=1 cal/g-° C.), temperature rise for a 2.5 Mrad dose is as follows (for a biological graft on a glass mandrel):

$$\frac{2.39 \text{ calories/gram}}{1.0 \text{ calories/gram} - ° \text{ C.}} \times 2.5 = 6.0° \text{ C.}$$

For a vascular graft on polycarbonate mandrel (specific heat=0.28 cal/g-° C.) a greater rise in temperature can be expected:

$$\frac{2.39 \text{ calories/gram}}{0.28 \text{ calories/gram} - ° \text{ C.}} \times 2.5 = 21.3° \text{ C.}$$

Given that the ambient temperature of a typical E-beam facility is approximately 20° C., the maximum theoretical final temperature of the polycarbonate mandrel would be approximately 41° C. The ambient temperature of a typical gamma cell facility on the other hand, is in excess of 38° C. The final temperature therefore, could reach approximately 59° C. Furthermore, an exposure time at this temperature would be a number of hours, as opposed to a few minutes with E-beam.

BRIEF DESCRIPTION OF THE FIGURES

FIG. 6 0.1% Glutaraldehyde - Fixed Bovine Carotid Artery; Shrink Temperature and Glutaraldehyde Depletion FIG. 7 Orientation of Electron Beam Scanner and Conveyor FIG. 8 Shows the effects of E-beam radiation on pressure drop.

SPECIFIC DESCRIPTION OF THE INVENTION

Figure 1:
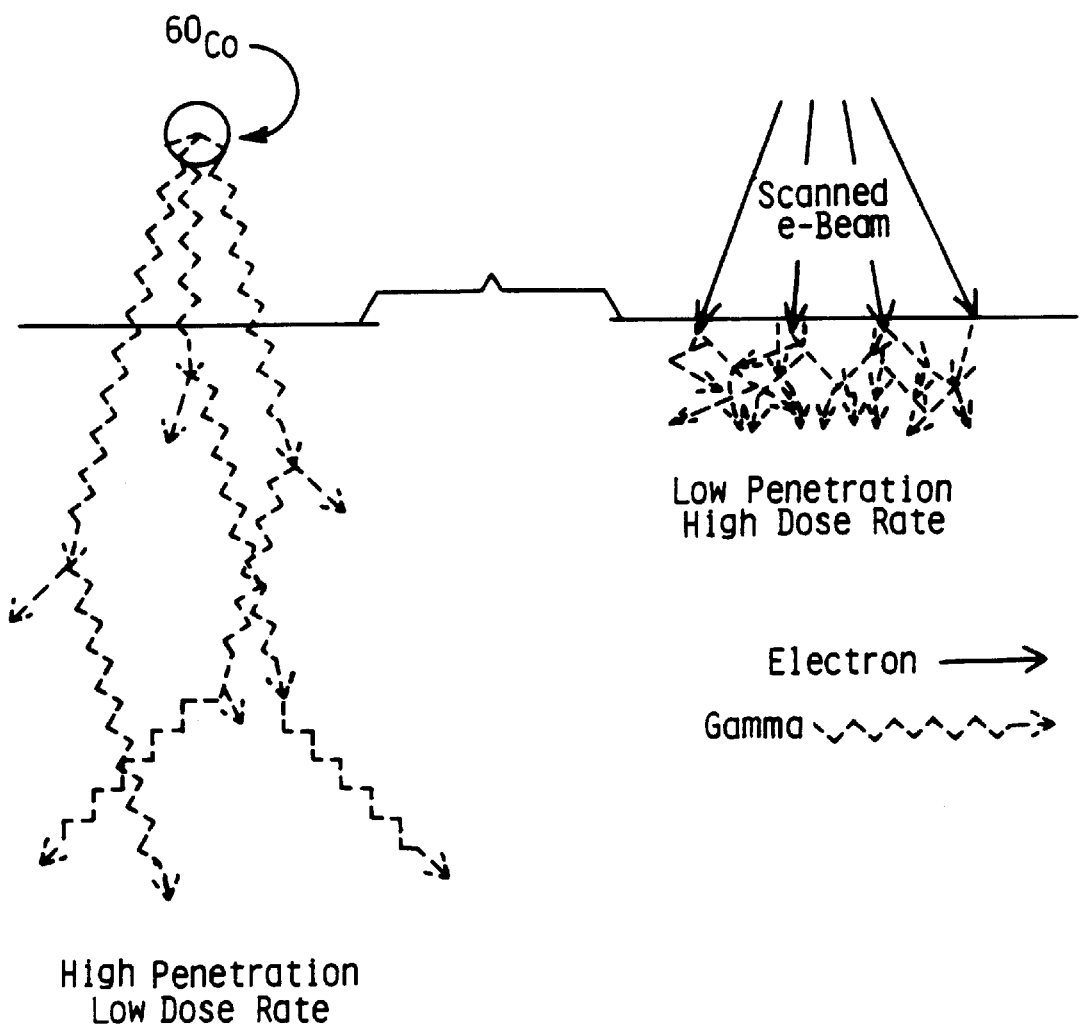
FIG. 1 Interaction of Gamma Rays and Electron Beams with Material

The present invention includes a method for sterilizing a biological tissue comprising directly exposing the tissue with a beam of accelerated electrons to sterilize the tissue. In a preferred embodiment, the sterilization is terminal sterilization.

The present invention also includes a method for sterilizing a biological tissue comprising irradiating a crosslinked tissue in a container with a beam of accelerated electrons to sterilize the tissue and container. In a preferred embodiment, the container is sealed prior to sterilization and the tissue and container are subjected to terminal sterilization.

The present invention also includes a sterilized biological tissue comprising a biological tissue treated according to a method of the invention.

The present invention also includes a sterilized biological tissue having improved performance characteristics.

The term "biological tissue" as used herein refers to a collagen-containing material which may be derived from different animal species, typically mammalian. The biological tissue is typically a soft tissue suitable for implantation, such as bioprosthetic tissue or the like, but the invention should not be limited thereby. Specific examples include, but are not limited to, heart valves, particularly porcine heart valves; aortic roots, walls, and/or leaflets; pericardium, preferably bovine pericardium or the like, and products derived from pericardium, such as a pericardial patch; connective tissue derived materials such as dura mater; homograft tissues, such as aortic homografts and saphenous bypass grafts; tendons, ligaments, skin patches; blood vessels, particularly bovine arteries and veins, and human umbilical tissue, such as veins; bone; and the like. Any other biologically-derived materials which are known, or become known, as being suitable for processing in accordance with the invention are within the contemplation of the invention.

In accordance with the invention, the biological tissue, explanted from its source may be processed in any suitable manner prior to exposure to a crosslinking agent.

The term "sterilization" as used herein refers to exposing the biological tissue to a sterilizing beam of accelerated electrons, i.e., an E-beam. The particle beam which comprises the E-beam preferably includes directional bombardment, i.e., bombardment from one direction only, and includes single-side or multiple-side irradiation.

The beam of accelerated particles may be provided by an electron accelerator capable of generating beams with energies of, for example, 10 mega electron-volts (MeV). As noted above, one skilled in the art will recognize that the energy of the beam effects only the depth of penetration, not the exposure time, and selecting the appropriate energy setting is dependent, in part, on the dimensions of the specific package or object.

In accordance with the invention, the amount of E-beam radiation is an amount sufficient to sterilize the biological tissue, and in some embodiments, an amount sufficient to sterilize the biological tissue packaged in its final container. One skilled in the art will recognize and be able to determine a sterilizing dose and time suitable for a particular tissue and based on the characteristics of the accelerator being used.

Typically, the biological tissue is subjected to a one-sided exposure to the electron beam until a sterilizing dose of radiation is absorbed. Absorbed dose of radiation is expressed in terms of kilograys (kGy). One kilogray is equal to one thousand joules of energy deposited per kilogram of material. For example, the biological tissue may be irradiated until a dose of approximately 25 kGy or more is achieved. For example, the FDA presently requires a dose of 25 kGy or greater for the sterilization of medical products. For the present invention, while upper and lower limits on the sterilizing dose have not yet been determined, sterilizing doses of greater than 25 kGy have been found effective, typically from about 25 kGy to about 28 kGy. In a preferred embodiment of the invention, the biological material is subjected to a one-sided top exposure to an electron beam until a top surface dose of approximately 25 to 28 kGy is achieved.

Irradiation may be carried out in a conventional manner, i.e. by placing the biological tissue in a suitable container, e.g., a glass or plastic container, and exposing the tissue to the electrons. For example, the biological tissue may be placed on a conveyor which then passes through the electron beam. Typically, the time of exposure to the beam may be proportional to the dimensions of the biological tissue. For example, a single row of heart valves (approximately eight valves) can be irradiated in approximately one minute, based upon a conveyor speed of 0.1 cm per second and a valve jar 5.5 cm in diameter.

Effective sterilization may be easily determined using conventional microbiological techniques, such as for example, the inclusion of suitable biological indicators in the radiation batch or contacting the tissue with a culture medium and incubating the medium to determine sterility of the tissue. Dose may also be determined with the use of radiochromic dye films. Such films are calibrated, usually in a gamma field, by reference to a national standard.

Degradation of the biological tissue by irradiation may also be determined using well known and conventional tests and criteria, e.g. reduction in shrink temperature, $T_s$; susceptibility to enzyme attack, e.g. collagenase; extractability of degradation products, e.g. collagen fragments; and decrease in physical properties such as tensile strength.

In accordance with an embodiment of the present invention; the biological tissue may be crosslinked prior to irradiation. Any crosslinking reagent may be used, preferably a reagent which stabilizes the tissue against subsequent in vivo enzymatic degradation, typically by crosslinking collagen in and on the biological tissue. Suitable crosslinking reagents include, but are not limited to glyoxal, formaldehyde, and glutaraldehyde. The preferred crosslinking agent is glutaraldehyde.

The crosslinking can be carried out in any desired method. Many such methods are described in the prior art. Generally, the crosslinking step comprises immersing the tissue in a reagent solution for from a few minutes to several days depending upon the desired degree of crosslinking. The solution may include one or a number of crosslinking reagents, such as, for example, glutaraldehyde, formaldehyde, glyoxal, and/or dialdehyde starch. The rate of crosslinking reaction can be controlled by controlling the concentration of crosslinking reagent and, to a lesser extent, by controlling the pH and/or the temperature of the crosslinking reagent. For example, the concentration of glutaraldehyde may be from about 0.001% to 8.0% volume to volume (v/v), preferably less than about 0.1% v/v glutaraldehyde.

The solution is typically buffered with any suitable buffer. Suitable buffers for use in the practice of the invention are those buffers which have a buffering capacity sufficient to maintain a physiologically acceptable pH, e.g., a pH between about 6 and about 8, and do not cause any deleterious effects to the biomaterial or interfere with the treatment process. Exemplary buffers include, but are not limited to phosphate-buffered saline (PBS), and organic buffers, such as N-(2-hydroxyethyl)piperazine-N'-(2-ethanesulfonic acid) [HEPES] or morpholine propanesulphonic acid (MOPS); and buffers which include borate, bicarbonate, carbonate, cacodylate, or citrate. In a preferred embodiment the solution is non-phosphate buffered, more preferably, citrate buffered at pH 6.4 or HEPES buffered at pH 7.4. Time and concentration are, of course, related and considerable variation in both are well known in the art.

In a typical protocol according to the invention, the biological tissue may be exposed to the fixing solution for a time and at a temperature sufficient to induce crosslinking of the collagen in and on the biological tissue. For example, the biological tissue may be exposed to a buffered glutaraldehyde solution from about 4° C. to about 37° C., preferably at about 20° C.; at a pH from about 6 to about 8, preferably 6.3 to 6.5; and for a period up to about 10 days, preferably from about 2 to about 5 days.

In accordance with the invention, one skilled in the art will recognize that certain parameters in the treatment protocol may be varied according to achieve a particular purpose. These parameters include, but are not limited to glutaraldehyde concentration and solution composition, pH and ionic strength, time and temperature of biological tissue exposure to glutaraldehyde, the ratio of tissue to volume of solution, and the biological tissue configuration during the initial fixation.

An embodiment of the invention may include exposing the crosslinked biomaterial to one or more bioburden reduction agents, typically for up to about 10 hours, preferably for about 2 to about 4 hours. For example, a porcine heart valve treated with glutaraldehyde as noted above may then be exposed to a buffered solution containing 1–5% glutaraldehyde, 1–6% formaldehyde, and 15–25% ethanol. Typical buffers include PBS, HEPES, and citrate buffers.

In accordance with an embodiment of the invention, the biomaterial, treated with glutaraldehyde as noted above, may then be exposed to one or more reagents designed to reduce or inhibit calcification of the biomaterial after implantation. For example, the crosslinked biomaterial may be exposed to an alcohol and/or an aluminum salt in order to reduce or inhibit calcification. In an exemplary process, the crosslinked biomaterial may be immersed in a solution containing greater than about 50% of a lower aliphatic alcohol such as ethanol for a period sufficient to render the biomaterial resistant to calcification, typically up to about 96 hours.

Typically, the crosslinked biological tissue is then rinsed, using, for example, any suitable rinsing or laving material. In a preferred embodiment, the rinsing agent is sterile, physiological saline.

The tissue may be rinsed with many volumes of sterile, physiological saline over a period of approximately 24 hours, or until the concentration of residual processing chemicals in the tissue are below levels which are considered to be toxic (approximately 1 ppm).

The biological tissue may then be placed or packaged in a container. In accordance with a preferred embodiment of the invention, the biological tissue is packaged and sealed, in physiological saline, in its final container prior to terminal sterilization. Packaging preferably means placing in a container suitable for storage and/or shipping.

The container may be constructed of glass or polymeric plastic. Suitable plastic materials include polyethylene; acrylates such as polymethyl methacrylate and polymethyl acrylate; polymethyl pentene-1; polyvinyl chloride; vinyl chloride-vinylidene chloride copolymers; polypropylene; urea-formaldehyde copolymer; melamine-formaldehyde copolymer; polystyrene; polyamide; polytetrafluoroethylene; polyfluorotrichloroethylene; polycarbonates; polyesters; phenol-formaldehyde resins; polyvinyl butyryl; cellulose acetate; cellulose acetate propionate; ethyl cellulose; polyoxymethylene; and polyacrylonitrile. In a preferred embodiment, the container is constructed of polypropylene, polyethylene, and/or epoxies. It is intended that the invention should not be limited by the type of container and seal being employed; other materials may be used, as well as mixtures, blends, and/or copolymers of any of the above.

The crosslinked, packaged biological tissue may then be sterilized, as noted above, or it may be stored for up to about a year or more prior to sterilization.

In accordance with the invention, storage includes long term storage, e.g., six months, twelve months, or for up to five years or more.

Some conventional techniques use glutaraldehyde as a sterilization agent in the packaged product sent to the surgeon. Such sterilization agents must be rinsed from the tissue prior to implantation. However, some of the embodiments according to the invention provide a product that requires no rinse prior to implantation. Residual chemicals, such as glutaraldehyde, used in the pre-packaging processing of the biological tissue are removed from the product prior to packaging, and the packaged tissue is terminally sterilized.

The present invention also includes a biological tissue which has been sterilized using E-beam radiation and has improved hemodynamic properties. In a preferred embodiment of the invention, the biological tissue is crosslinked with a suitable crosslinking reagent and irradiated with a beam of accelerated electrons to sterilize the tissue. As noted above, the tissue may be terminally sterilized after it has been sealed in a sterile container.

In accordance with the invention, tissues which have been exposed to E-beam radiation may be softer or more pliable, may exhibit a greater range of movement for some of its movable parts, e.g., the leaflets of a heart valve; and increases the biological tissue's long-term durability.

EXAMPLES

Example 1. Glutaraldehyde pre-treatment. Fresh tissue (e.g., blood vessels, hearts, heart valves, or pericardium) are procured from a local processing facility (bovine, porcine, ovine, etc.) and received in physiological saline (0.9% sodium chloride) on ice. The tissue is either dissected immediately or placed in fresh sterile saline and refrigerated overnight. Extraneous tissue such as adipose, skeletal muscle, myocardium, bone, trachea, etc., is carefully removed from the tissue of interest. The tissue is then again washed and immersed in fresh sterile saline.

Although this technology works to varying degrees at a range of glutaraldehyde concentrations, approximately 0.03% provides radioprotective properties and the crosslinking time fits reasonably well within a manufacturing schedule. For 10.0 liters of 50 mM citrate buffered 0.03% (v/v) glutaraldehyde:

Step 1)

A 50 mM citrate buffer solution is prepared per the following formula (10 liters): To 9.0 liters of sterile, de-ionized water, add: 140.0 grams of Sodium Citrate 5.0 grams of Citric Acid Monobasic 38.6 grams of Sodium Chloride Bring the volume of the solution up to 10.0 liters with sterile, de-ionized water Step 2)

To 9.0 liters of the 50 mM citrate buffer solution prepared in Step 1, add 6.0 milliliters of 50% Biological Grade Glutaraldehyde Bring the solution volume up to 10.0 liters using the 50mM citrate buffer solution prepared in Step 1.

Step 3)

Adjust the pH of the solution to 6.40±0.05 using hydrochloric acid or sodium hydroxide.

Figure 5:
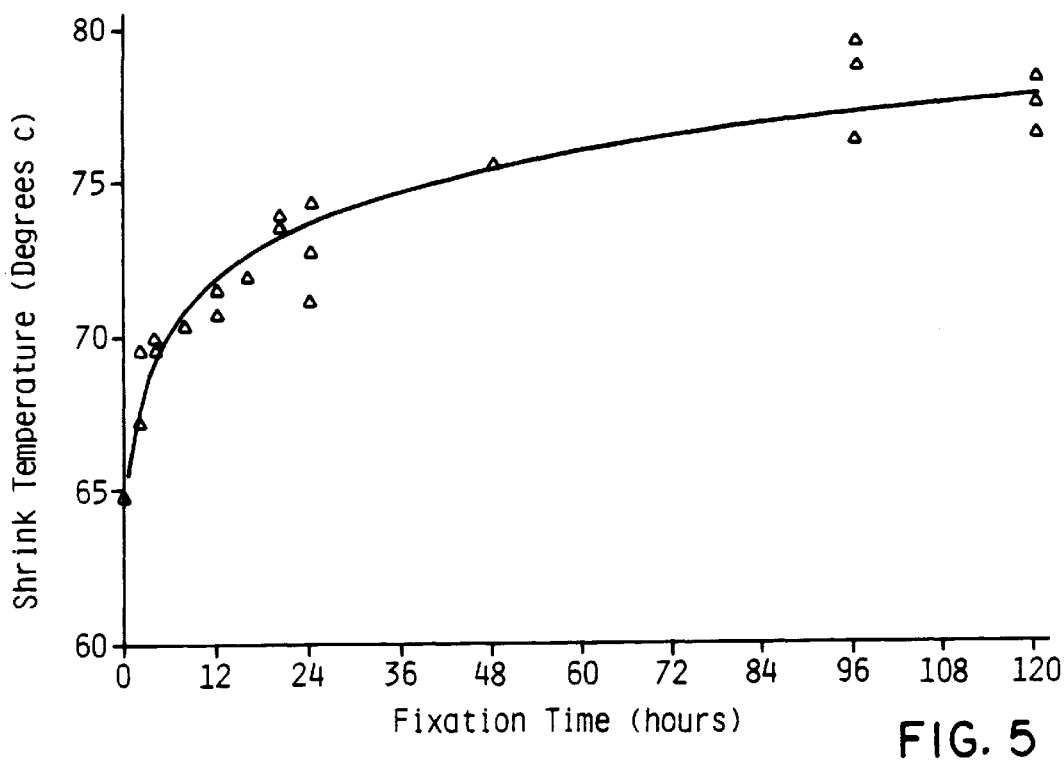
FIG. 5 Bovine Pericardium Shrink Temperature - 0.01% Glutaraldehyde
Figure 6:
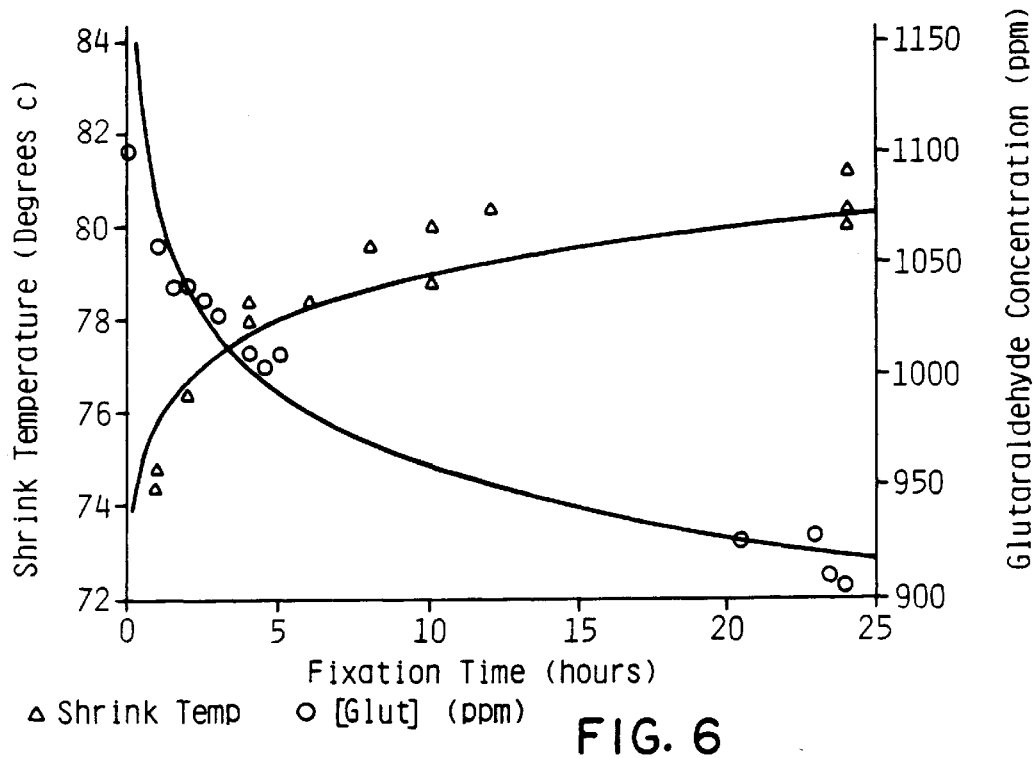
Figure 7:
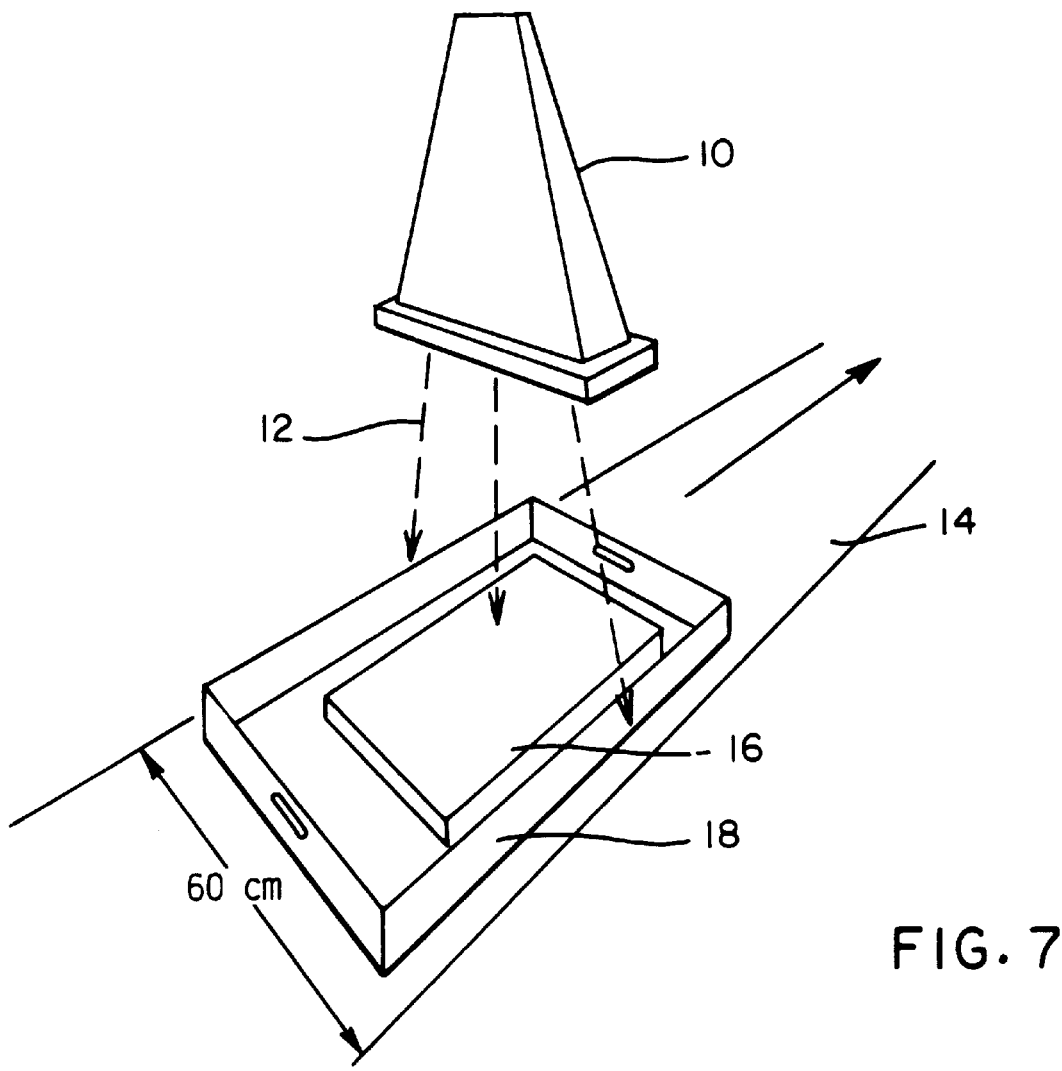

The tissue is then immersed in the glutaraldehyde solution, at room temperature (20–25° C.) for the crosslinking reaction. As fixation time progresses, the number of crosslinks increases, as shown in the form of a shrink temperature curve (See FIG. 5). The concentration of glutaraldehyde in solution decreases as it is consumed by the tissue in the form of polyglutaraldehyde crosslinks. Therefore, it may be necessary to replenish the fixation solution at intervals throughout the crosslinking reaction. Because a majority of the crosslinks are formed early, it is recommended to change the solution approximately eight hours following the onset of the reaction, then daily thereafter.

The exposure of tissue to the glutaraldehyde solution proceeds for a period of time ranging from 24 to 120 hours, depending on the concentration of glutaraldehyde in the solution. In general, a high glutaraldehyde concentration corresponds to a short fixation time; a low glutaraldehyde concentration corresponds to a long fixation time. For a 0.03% solution, an exposure time of approximately 72 hours is necessary to maximize the crosslink density within the interstices of the tissue. This corresponds to a shrink temperature of approximately 80–89° C., depending on the type of tissue used.

When the crosslinking reaction has ended, the tissue is submersed in a solution containing 2% (v/v) glutaraldehyde, 3% (v/v) formaldehyde, and 20% (v/v) ethyl alcohol. This multi-component sterilant reduces any residual bioburden on the tissue prior to rinsing and packaging.

The tissue is then thoroughly rinsed with sufficient sterile saline to remove all processing chemicals. This typically requires applying four or five 10 liter aliquots over a 24-hour period. The exposure time must be watched carefully, since diffusion of residuals from the tissue is a time-dependent phenomenon. After the final rinse, the tissue is placed in a sterile container (valve jar, vascular graft vial, etc.) and filled with sterile saline. The package is then permanently sealed. Note: all manipulations of the tissue subsequent to the bioburden reduction process with the multi-component sterilant should be performed as aseptically as possible to minimize the extent of contamination prior to E-beam sterilization.

Example 2. E-beam radiation. Porcine aortic leaflets were crosslinked with 0.01%, 0.1%, or 0.6% glutaraldehyde using the protocol described in Example 1. The non-control leaflets were then exposed to 25 kGy E-beam radiation. Table 1 is a summary of the data from an experiment designed to demonstrate how collagen integrity is preserved by E-beam irradiation of tissues crosslinked in low-concentration glutaraldehyde. As shown in Table 1, a reduction in shrink temperature was shown for tissues crosslinked in low-concentration glutaraldehyde and sterilized by exposure to E-beam radiation.

TABLE 1

Shrink Temperature (° C.): Glutaraldehyde Crosslinked Porcine Aortic Leaflets Pre- and Post-Radiation (25 kGy)

| Sample | 0.01% Glutaraldehyde | | 0.1% Glutaraldehyde | | 0.6% Glutaraldehyde | |
|---|---|---|---|---|---|---|
| | Control | E-Beam | Control | E-Beam | Control | E-Beam |
| 1 | 87 | 82 | 86 | 81 | 87 | 82 |
| 2 | 86 | 82 | 87 | 81 | 88 | 82 |
| 3 | 86 | 81 | 86 | 81 | 87 | 82 |
| 4 | 86 | 82 | 87 | 82 | 88 | 82 |
| 5 | | 81 | 87 | 81 | 88 | 82 |
| 6 | | | 86 | 81 | 88 | 82 |
| 7 | | | 86 | 81 | | |
| 8 | | | 86 | 81 | | |
| 9 | | | 87 | 82 | | |
| 10 | | | | 82 | | |
| 11 | | | | 81 | | |
| Mean | 86 | 82 | 86 | 81 | 88 | 82 |
| Std | 0.5 | 0.5 | 0.5 | 0.5 | 0.5 | 0 |
| Δ | | 4 | | 5 | | 6 |

Figure 2:
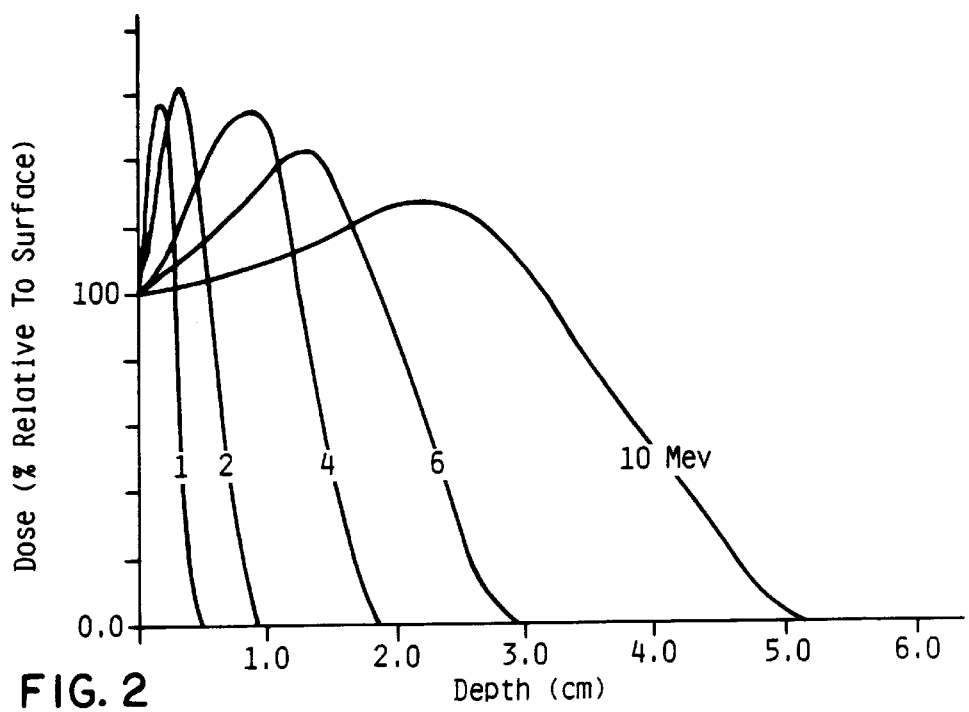
FIG. 2 Increase in Dose With Depth of E-Beam Penetration

Example 3. For 10 MeV electrons, the ratio of maximum to minimum dose is typically about 1.3:1. This phenomenon is illustrated in FIG. 2 which shows the distribution of dose with depth when a material is irradiated with electrons at different energy levels.

For 10 MeV electrons in unit specific gravity material, the maximum dose is achieved at a depth of about 2.3 cm. The dose is about the same as the dose at the surface at a depth of 3 cm, and is practically zero at a depth of 5 cm. For 10 MeV electrons the maximum dose is about 1.33 of the dose at the entrance and exit surfaces, or a ratio of about 1.3:1.

The same entrance and exit dose is achieved for materials with an areal (unit density) of about 3.0 g/cm$^2$ for single-sided irradiation with 10 MeV electrons. However, the primary-beam causes additional charged particle fluence of electrons in the material. The result is a buildup of dose within the material, particularly in the center. For example, if the surface dose is about 10 kGy and the exit dose is about 10 kGy, the build-up in the center may be about 13 kGy. This contrasts sharply with gamma irradiation, in which the gamma rays transfer energy by Compton scattering collisions with atomic electrons. Here the probability for Compton scattering is low, allowing the gamma rays to penetrate relatively long distances in materials before scattering. Therefore, gamma rays deposit energy in materials over large volumes so that penetration is high, but dose rates are low (typically about 20 kGy/hr maximum, 4 kGy/hr average; 50 cm depth in unit-density material).

Example 4. An experiment was performed to calculate the maximum dose experienced inside a biological vascular graft package due to build-up. Bovine carotid arteries were cleaned and crosslinked with 50 mM citrate-buffered 2% glutaraldehyde. The grafts were irradiated, immersed in saline inside their glass tubes, with 9.2±0.01 MeV electrons from the I-10/1 Linac at the Whiteshell Laboratories. The tubes were laid on their sides and exposed to the scanned beam from above. Several dose studies with radiochromic dye dosimeters (Far West Technology) placed above and below the tubes showed that the dose on top of and immediately underneath the tubes was the same to within a few percent. This indicates that the glass tubes and their contents are approximately the optimum thickness for single-sided irradiation with electrons of this energy (~3g·cm$^2$). This means that the dose at some points within the tubes could be as much as 33% higher.

A sheet of red polymethylmethacrylate (red PMMA or red acrylic) was placed under one set of three tubes, which were wrapped in plastic bubble wrap to prevent mechanical damage. The tubes and PMMA were irradiated in the same way as before with 9.2 MeV electrons.

The PMMA darkened in proportion to the dose it received. Therefore, if the calibration curve relating the absorption to dose is known the dose distribution in the plane of the red acrylic sheet may be determined. Normally, only the relative dose distribution is of interest.

Absorption and scattering of electrons by the overlaying tubes was plainly visible in the PMMA following irradiation. A computer controlled travelling densitometer (Therescan, Theratronics Limited, Kanata, Ontario) was used, first to scan across the PMMA and then to plot isodose curves over the surface of the PMMA sheet.

Figure 3:
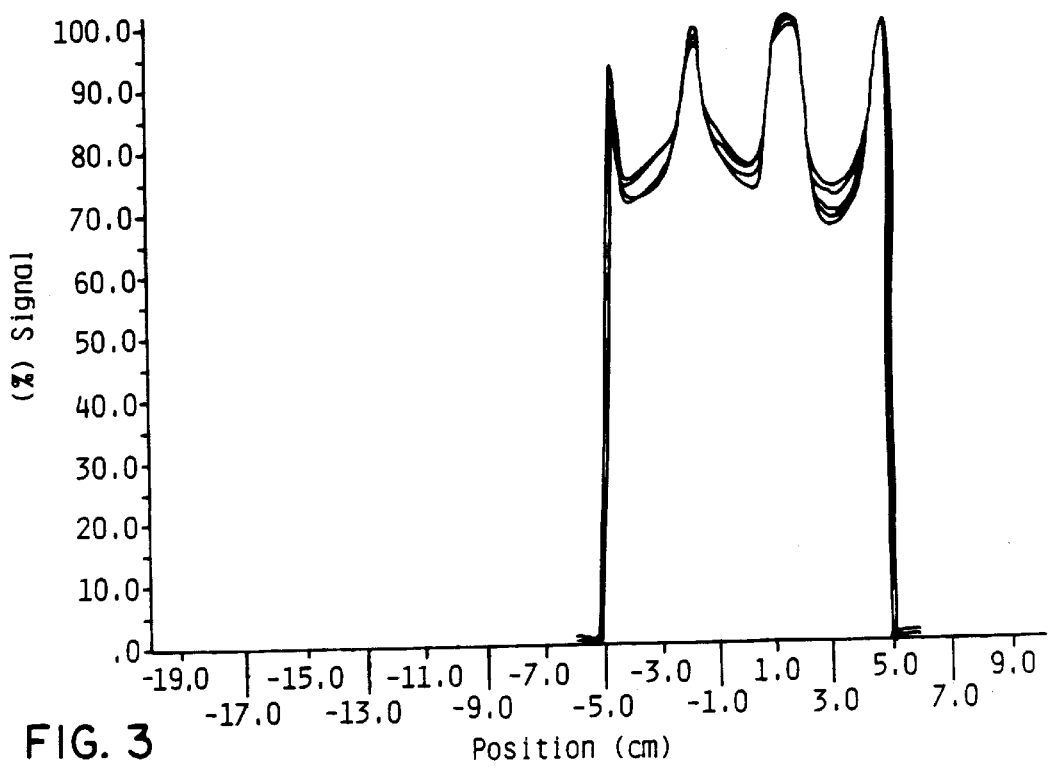
FIG. 3 Position vs. %-Signal

FIG. 3 shows densitometer traces across the PMMA sheet perpendicular to the tubes. These transect the PMMA sheet at five different points along its length. The relative light absorbance, which is proportional to dose, is shown on the legend to the left in FIG. 3. This indicated a maximum to minimum dose ration of 1.0 to 0.67, or about 1.5.

Figure 4:
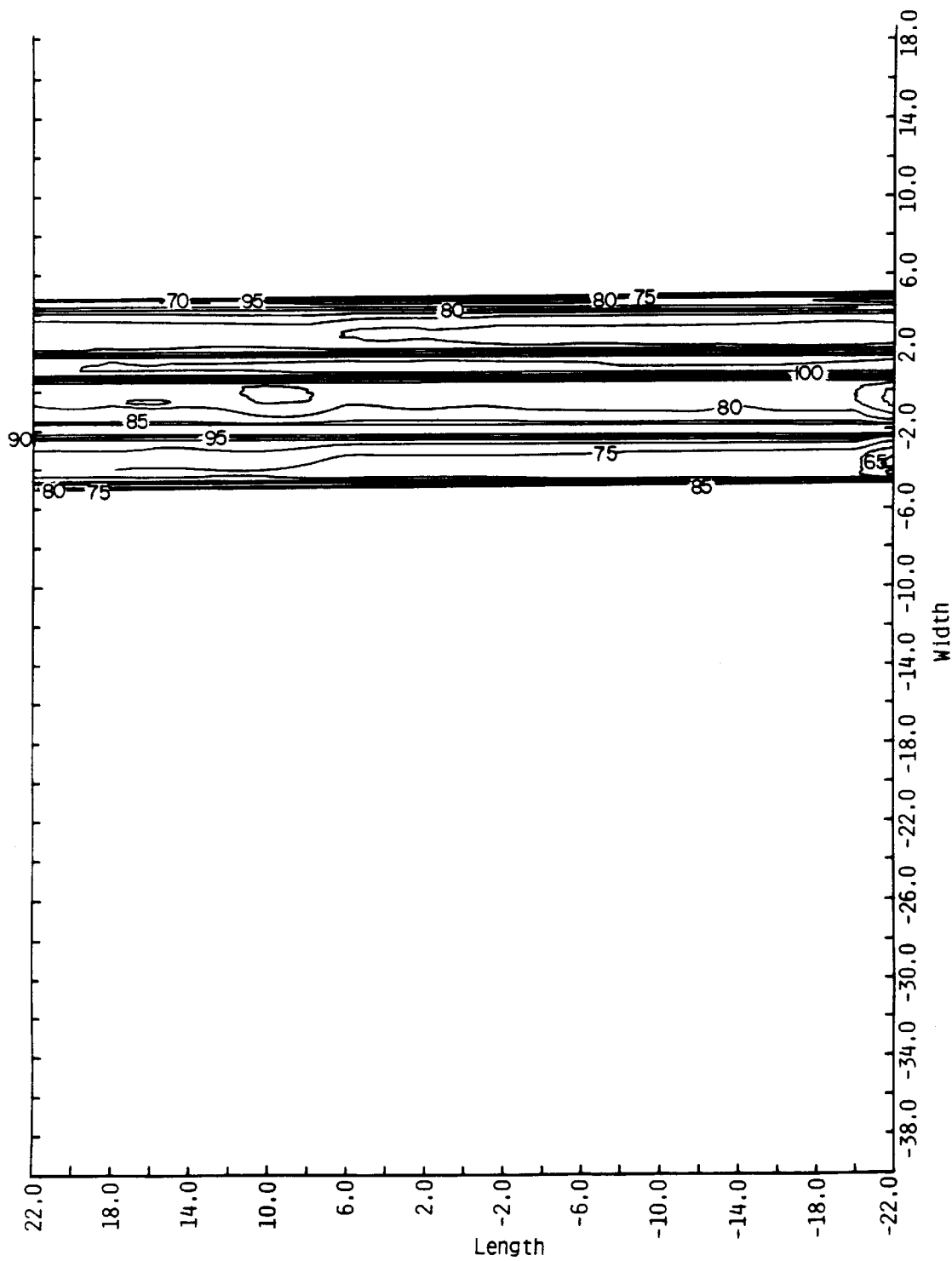
FIG. 4 Therascan Contour Depiction of BPM™ Graft

Isodose contours for the same PMMA sheet are plotted in FIG. 4. Each of the five transects in FIG. 3 were normalized to maximum absorbance for that transect. The isodose contours are normalized to the maximum absorbance at any point on the sheet. The lowest dose contour surrounds a small area in the lower left of the figure. This contour received 65% of the maximum does, so the max/min ration is 1.54.

The results of the study with PMMA do not contradict the study with the Far West dosimeters, which indicated that the dose immediately above and below the tubes is about equal. In fact, PMMA results indicate that, except for a few cases, the dose registered in the PMMA between the tubes is approximately the maximum 133% of the dose underneath the tubes due to buildup in the packing between the tubes.

The exceptional case may be important. The 65% maximum dose contour surrounds an area of the PMMA which was underneath the cap of the tube. In this case, the glass of the tube is thicker to accommodate the screw tap and the cap itself adds to the amount of material the electrons must penetrate. Moreover, at these points the scanned beam is directed at a slight angle from the perpendicular to the axis of the tube and must penetrate slightly more material in the slant-wise direction. This does not necessarily mean that the inside of the tube is not getting sufficient radiation to result in sterilization.

In summary, the grafts, as presently packaged and irradiated in glass tubes, are receiving approximately equal dose on the upper and lower surfaces of the tubes and about 133% of the dose on the upper surface inside the tubes at the location of the grafts. The exception to this is that the dose under the caps appear to be approximately 65% of the maximum does received by the grafts, or about 86% of the dose at the upper surface of the tubes. If the top surface were to receive 25 kGy, the dose to the grafts could be as high as 33.3 kGy and the dose under the cap end of the tubes would be about 21 kGy.

Figure 8:
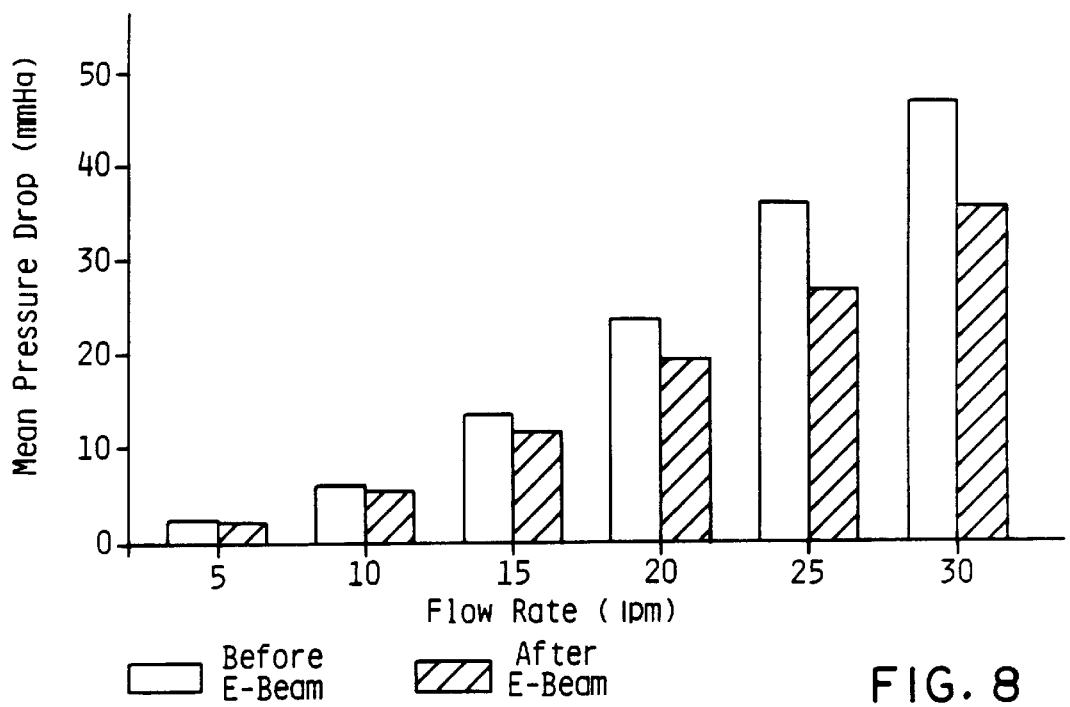
Figure 9:
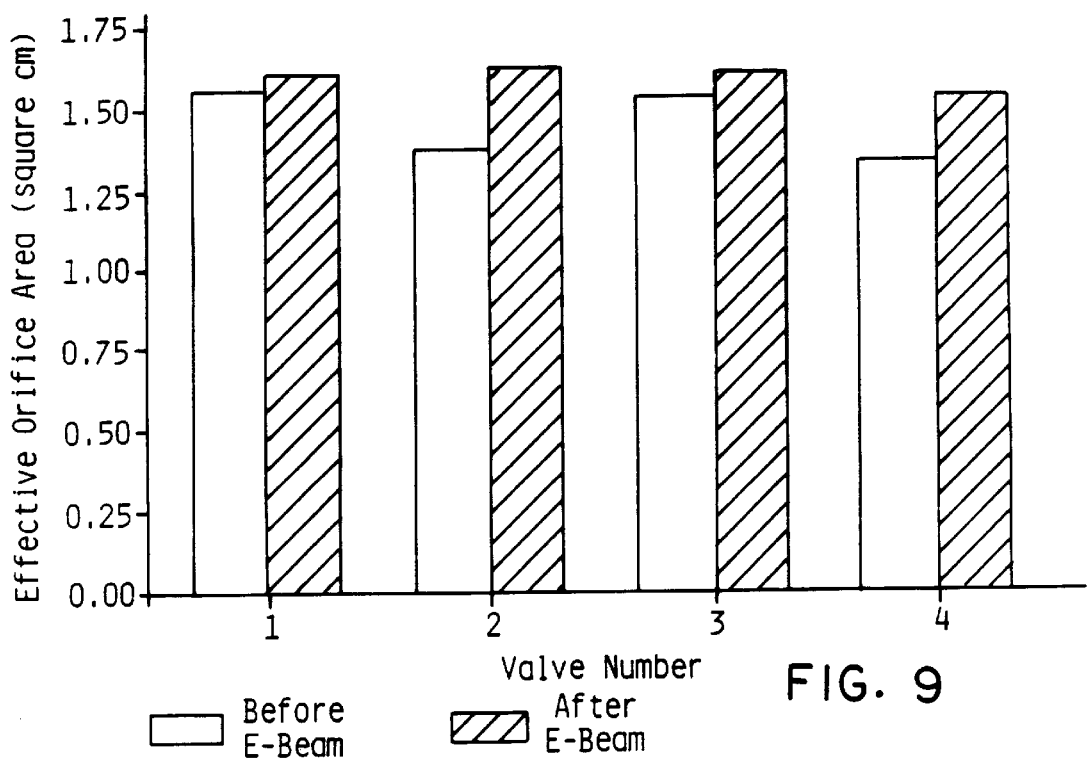
FIG. 9 Shows the effects of E-beam on effective orifice area.

Example 5. Experiments have shown that glutaraldehyde-crosslinked tissue, exposed to E-beam radiation, exhibits enhanced hemodynamic performance characteristics, such as flexibility. Evidence of increased flexibility is provided by measuring pressure drop across the heart valve (the change in pressure from the inflow side of the valve to the outflow side), as shown in FIG. 8. Enhanced flexibility is also shown by measuring the effective orifice area, the cross sectional area through which blood flows, as shown in FIG. 9. These tests show that exposing heart valves to E-beam radiation results in softer leaflets which tend to open more readily and to a greater extent than non-irradiated valves. This provides both short-term and long-term benefits to the recipient because a larger effective orifice area results in greater cardiac output and therefore, an increase in efficiency of cardiac activity and a decreased tendency to develop cuspal fractures leading to eventual calcification and valve failure.

Eight heart valves were glutaraldehyde crosslinked and exposed to E-beam radiation as shown in Examples 1 and 2. The pressure drop across the heart valve before subjecting the heart valve to E-beam radiation was compared to the pressure drop after subjecting the heart valve to E-beam radiation. FIG. 8 graphically illustrates that the pressure drop decreases when tested on a steady state in vitro flow tester. As a reference point, the pressure drop for a straight, unobstructed tube would be zero.

FIG. 9 compares the effective orifice area before and after exposing the heart valve with E-beam radiation, and shows that the effective orifice area increases following E-beam radiation.

Effective Orifice Area determinations were made by placing test valves in a Pulse Duplicator system. The Pulse Duplicator is capable of calculating a number of valve-related functions by measuring pressures and flow rates at strategic locations within a simulated heart containing the test valve.

Effective Orifice Area (EOA) is defined as follows:

$EOA=Q_{rms}/(51.6 \sqrt{\Delta P})$, expressed in $cm^2$, where $Q_{rms}=$ root mean square flow rate obtained during the period of positive pressure drop, in ml/second $\Delta P$=mean positive pressure drop, in mm Hg The theory behind enhanced hemodynamics in irradiated tissue heart valves involves the disruption of molecular bonds which hold the collagen triple helix intact. The intramolecular crosslinks offered by this technology serve as reenforcement to the collagen backbone as its own structural frame work is weakened by the radiation. A dose of 25 kGy, in the presence of sufficient intramolecular crosslinks, weakens the protein framework to sufficiently render the tissue more flexible, yet the tissue performance improves.

Similar results have been obtained every time these two experiments were repeated. While the exact mechanism is unknown, it is theorized that a scission reaction occurs within the collagen molecule. Bonds that hold the collagen chain together appear to be broken when subjecting a tissue to E-beam radiation. However, the presence of intramolecular glutaraldehyde crosslinks appears to keep the primary structure of the collagen molecule intact, thus maintaining the integrity of the softened tissue.

Example 6. The major criticism of radiation as a sterilization method for biological tissues is its effect on long-term durability of the product. The FDA currently requires that tissue valves demonstrate the ability to withstand 200 million cardiac cycles on an accelerated wear tester. This translates to approximately five years of real time. At some point in the future, 380 million cycles of the same testing may be required.

We performed an experiment to determine the effects of E-beam radiation on the wear-resistance of tissue valves. Four groups of valves were tested:

| | |
|---|---|
| Group 1 | Crosslinked in 0.03% glutaraldehyde; stored in 0.5% glutaraldehyde (E-beam negative control). |
| Group 2 | Crosslinked in 0.03% glutaraldehyde; rinsed for removal of residuals; stored in 0.9% sodium chloride; E-beam sterilized, 25 kGy. |
| Group 3 | Crosslinked in 0.03% glutaraldehyde; treated with anticalcification process; rinsed for removal of residuals; stored in 0.9% sodium chloride; E-beam sterilized, 25 kGy. |
| Group 4 | Crosslinked in 0.5% glutaraldehyde; rinsed for removal of residuals; stored in 0.9% sodium chloride; E-beam sterilized, 25 kGy (concentration negative control). |

Results of this experiment are located in Table 2 below. These results clearly indicate that, compared to control valves (Groups 1 and 4), exposing the tissue valves to E-beam radiation does not have a negative effect on durability after in vitro testing at 389 million cardiac cycles. The group with the best wear data, in fact, was the group that had been exposed to E-beam after a treatment for anticalcification.

TABLE 2

Results of 389 Million Cycles Accelerated Wear Testing: E-Beam v. No E-Beam

| Treatment | Number of Valves | Summary of Anomalies |
|---|---|---|
| Group 1 | 4 | 6 large holes (>1 mm) |
| | | 2 small holes (≦1 mm) |
| | | 2 large tears in leaflets (2–6 mm) |
| | | 1 small abrasion |
| | | 1 valve with no observed wear |
| Group 2 | 4 | 2 large holes |
| | | 5 small holes |
| | | 1 small abrasion |
| | | 1 valve with no observed wear |
| Group 3 | 6 | 3 small holes |
| | | 4 valves with no observed wear |
| Group 4 | 3 | 3 holes (0.5 to 3 mm) |
| | | 2 valves with no observed wear |

Example 7. To determine if there is a significant difference in the response of Bacillus pumilus to equivalent doses of gamma and E-beam radiation, a population of B. pumilus was irradiated in liquid suspension with gamma and E-beam radiation, then the surviving fraction of the population at a series of doses was determined. At a dose of 6 kGy, there was approximately 100 times more surviving organisms that were gamma irradiated than were E-beam irradiated (surviving fractions of $10^{-4}$ vs. $10^2$, respectively).

Example 8. There has always been some concern as to the effects of E-beam radiation on the microstructure of tissue. The issue of preservation of "collagen crimp", or the natural waviness of collagen is very important in providing superior performance and durability in any bioprosthetic valve. An experiment was performed to examine the effects of dynamic, or pulsatile fixation (with and without E-beam), on the morphology of porcine aortic valve leaflets.

Three groups of tissue were prepared for this experiment. One group contained tissue crosslinked with 0.03% glutaraldehyde in a pulsatile fashion, rinsed of all residuals, and sterilized with 25 kGy electrons. A second group was treated the same as the first group, but was not sterilized with E-beam radiation. The control group contained leaflets that most closely represented "natural" valve leaflets: crosslinked under "zero-pressure" conditions to maintain integrity of all cellular and acellular components.

Each group of leaflets, forwarded to an independent agency for evaluation, were found to have virtually indistinguishable morphology, and that there was no consistent effect of either dynamic fixation or of a sterilizing dose of ionizing radiation on the structure of the valves. Furthermore, there were no consistent differences among the valves in any of the following: collagen crimp, collagen crispness, internal valve spaces, amorphous extracellular matrix, or cellular autolytic features.

Example 9. The increase in temperature during the E-beam process was measured. Thermocouple leads were inserted through small holes drilled in the caps of two packages containing a biological vascular graft packaged in saline. The leads were then positioned between the graft tissue and the polycarbonate mandrel to measure the temperature at the mandrel/tissue interface during E-beam exposure. The results of the experiment indicate that the temperature rise was approximately 7° C. over ambient temperature, resulting in a final temperature of approximately 27° C.

Examples 10 and 11. The effects of glutaraldehyde fixation on bovine vascular tissue and possible destabilization by ionizing radiation can be evaluated be determining the denaturation temperature of the substrate. A convenient method of determining this value is by measuring the shrink temperature ($T_s$) of the tissue, which increases with an increasing number of crosslinks. Glutaraldehyde crosslinked vascular tissue, following exposure to ionizing radiation, has demonstrated a loss in thermal stability. In previous studies, a decrease in $T_s$ of approximately 6° C. had been noted following a 2.5 Mrad dose of electron beam (E-beam) irradiation. Several modifications to the storage solution including the use of radioprotectant compounds sodium thioglycolate and mercaptoethylamine (MEA), catalase (a hydrogen peroxide scavenger), and alternative buffers, have in some cases minimized the $T_s$ depression after 2.5 Mrad of radiation exposure. The objective of these studies was to test and identify one or more methods of packaging and radiation sterilizing biological tissue while keeping tissue damage to a minimum.

Example 10. Twenty median artery grafts were ficin digested and glutaraldehyde crosslinked as follows: the grafts were crosslinked with 0.01% glutaraldehyde for 112 hours, and then pre-sterilized for five hours in 2% glutaraldehyde. The grafts were then aseptically packaged in sterile 0.9% sodium chloride and allowed to remain on the shelf for a period of 9 days for diffusion of residual glutaraldehyde from the tissue. Grafts were then placed into a sterile tank containing 16 liters of sterile saline for further rinsing of glutaraldehyde residuals. Following a 3-hour rinse in sterile saline, the grafts were packaged for E-beam sterilization. Each graft was placed in a polyethylene pouch and filled with a 50 mM citrate-buffered saline solution at pH 6.4 and radioprotectant additives as follows:

5 packages - 0.01M sodium thioglycolate
5 packages - 0.01M MEA
5 packages - 0.1M MEA
5 packages - control (citrate-buffered saline only)

The 15 non-control packages were then exposed to 2.5 Mrad E-beam irradiation.

Traditionally, radioprotectants have been administered to animals or culture media immediately prior to irradiation to minimize its effects. Most of the compounds used in early radioprotection contained either —SH or —NH$_2$ groups because of their ability to absorb energy emitted by radiation sources. The exact mechanism of protection, however, is still unknown. In the early 1950s, approximately three thousand compounds were tested for effectiveness as radioprotectants and for toxicity. Of those tested, β-mercaptoethylamine (MEA or cysteamine) was found to be the most effective as an in situ radioprotectant used with tumor radiotherapy. The compound has been administered intravenously to humans in doses of up to 500 mg, twice per day, for thirty days with no ill effects.

Another thiol compound, sodium thioglycolate, has been used as a radioprotectant with the gamma sterilization of culture media to eliminate the need for aseptic filling. Sodium thioglycolate has been used at a level of 0.01M. It was preferred over other agents because it is nontoxic and does not significantly reduce the efficiency of the sterilization.

As the $T_s$ results displayed in Table 3 suggest, there was not much protection afforded by either of the radioprotective agents. The mean $T_s$ value obtained for the 0.1M MEA (75.6° C.) was, in fact, lower than the samples with 0.01M MEA (77.5° C.).

TABLE 3

Shrink Temperature Results - Example 10

$T_s$ (° C.) after 2.5 Mrad E-Beam

| Sample Number | Controls (no E-beam) | No Protection (Historical) | 0.01 M Thio-glycolate | 0.01 M MEA | 0.1 M MEA |
|---|---|---|---|---|---|
| 1A | 81.6 | 77.2 | 78.4 | 77.2 | 75.2 |
| 1B | 81.2 |  | 77.6 | 77.6 | 75.6 |
| 2A | 83.6 | 77.6 | 78.0 | 77.2 | 77.2 |
| 2B | 83.2 |  | 78.8 | 77.2 | 76.8 |
| 3A | 82.8 | 77.2 | 76.4 | 77.2 | 76.4 |
| 3B | 83.2 |  | 77.2 | 78.0 | 75.2 |
| 4A | 82.8 | 77.2 | 78.0 | 78.4 | 75.2 |
| 4B | 83.2 |  | 79.6 | 78.0 | 74.8 |
| 5A | 82.8 | 77.6 | 76.8 | 77.2 | 74.8 |
| 5B | 82.4 |  | 77.6 | 76.8 | 75.2 |
| 6 |  | 77.6 |  |  |  |
| Mean | 82.7 | 77.4 | 77.8 | 77.5 | 75.6 |
| Std. Dev. | 0.8 | 0.2 | 0.9 | 0.5 | 0.9 |
| Δ After E-beam (mean) | NA* | 5.3 | 4.9 | 5.2 | 7.1 |

*Not Applicable

Example 11. In this example a second batch of bovine median arteries, processed as in Example 10, was used for E-beam testing. The sodium thioglycolate concentration was increased from the previous batch from 0.01 to 0.1M. Catalase was also added to two of the test groups to decompose hydrogen peroxide (H$_2$O$_2$), a by-product of E-beam irradiation which may be deleterious to graft wall integrity. The concentration of H$_2$O$_2$ generated by ionizing radiation in polyethylene containers should theoretically be approximately $50 \times 10^{-6}$ moles per liter.

The following information was provided with the lot of catalase used in this study (Sigma, lot 100H3829, derived from *Aspergillus niger*):

24 mg protein/ml stock solution
7080 units enzyme/mg protein
1 unit catalase will decompose 1.0 μmole H$_2$O$_2$ per minute at pH 7.0

The buffer used in the storage solution was changed in this example from citrate to HEPES, (pH range of 7.2–7.4).

HEPES is a commonly-used biological buffer used to achieve this particular pH range. Based on $T_s$ results obtained with MEA in Example 10, it was not used in this phase of the study. Rather, the concentration of sodium thioglycolate was increased ten-fold to 0.1M. Damage occurring in radiation-sterilized culture media has been attributed to the formation or accumulation of peroxides. The damage to the collagen in or on this product, indicated by a decrease in $T_s$, may be caused by the same mechanism. The addition of the radiation-resistant enzyme catalase, which is a peroxide scavenger, has been shown to reduce H$_2$O$_2$.

As in Example 10, the use of thioglycolate, with and without the addition of catalase, provided minimal protection based on $T_s$ (means of 76.8° C. and 77.4° C. respectively). The group containing HEPES buffer, however, resulted in a mean $T_s$ value of 78.5° C., which is only 2.8 degrees lower than the control (no E-beam) value of 81.3° C. The data gathered in this phase of the study suggests that damage caused to the tissue could be minimized more effectively by buffering in the proper pH range than by using traditional radioprotective agents.

The following calculations were then applied to determine the amount of catalase necessary to decompose the H$_2$O$_2$ theoretically generated by the irradiation process (4.5 liters of packaging solution was needed for the batch):

Total amount of H$_2$O$_2$ generated in 4.5 L:

$$4.5L \times (50 \times 10^{-6} moles/L) = 2.25 \times 10^{-4} \text{ moles}$$

Units of catalase to decompose H$_2$O$_2$ in 4.5 L packaging solution:

$2.25 \times 10^{-4}$ moles (1 μmole/$10^{-6}$ mole)(1 unit catalase/1 μmole)=225 units Units of catalase per ml of stock solution:

7080 units/mg×24mg/ml stock solution=169,920 units/ml stock solution

Volume of stock solution necessary for 4.5 L packaging solution:

225 units (1 ml stock solution/169,920 units)=$1.3 \times 10^{-3}$ ml or approximately 2 μL stock catalase solution per 4.5 L packaging solution Units of catalase present in each graft package:

(2 μL stock solution/4.5 L packaging solution)(1 ml/1000 μL)(24 mg protein/ml) (0.15 L packaging solution/package)(7080 units catalase/mg protein) =11 units catalase/package (volume of catalase per package was rounded to 2 μL due to the limits of the measuring device)

The effectiveness of the radioprotectants was evaluated by $T_s$ testing. Four combinations of storage solutions were prepared as identified in Table 4 below:

TABLE 4

Test Groups - Example 11

| Group | Hepes | Thioglycolate | Catalase | E-Beam |
|---|---|---|---|---|
| 1 (A–G) | X |  |  | X |
| 2 (H–N) | X | X |  | X |
| 3 (O–U) | X | X | X | X |
| 4 (V–AB) | X | X | X |  |

Results of the $T_s$ analyses are displayed in Table 5 below:

TABLE 5

Shrink Temperature Results

| Group Number | $T_s$ (° C.) | | Δ Control |
|---|---|---|---|
| 1 (HEPES, E-beam, 2.5 Mrad) | 78.5 ± 0.6 | n = 7 | 2.8 |
| 2 (HEPES, Thioglycolate, E-beam, 2.5 Mrad) | 77.4 ± 0.8 | n = 7 | 3.9 |
| 3 (HEPES, Thioglycolate, Catalase, E-beam, 2.5 Mrad) | 76.8 ± 0.9 | n = 7 | 4.5 |
| 4 (HEPES, Thioglycolate, Catalase, no E-beam) control group | 81.3 ± 0.8 | n = 7 | N/A* |

*Not Applicable

Examples 12 and 13. Examples 12 and 13 involve the use of bovine pericardial tissue in minimizing the destructive effects of the radiation. Pericardium was used as a substitute for vascular tissue for these examples for the following reasons: much less preparation time is necessary and therefore, more samples may be prepared per batch, the tissue possesses a very high collagen content (approximately 90% versus 45% in the carotid and median arteries) which assures accurate and consistent results, and the results should be easily translated to vascular applications.

Example 12. In this Example, the tissue was evaluated after storage in various biological buffers without the addition of the radioprotective compounds noted in Example 11.

Four fresh bovine pericardial sacs were received in physiological saline (0.9% sodium chloride) on ice. The tissue was placed in fresh sterile saline and refrigerated overnight. Adipose tissue was carefully removed from the epicardial surfaces and they were again washed in sterile saline. One hundred thirty-three 2cm ×9cm sections, which represents the normal $T_s$ graft test sample size, were cut from the pericardial tissue. The samples were evenly divided between two large beakers, each containing 3 liters of 50 mM citrate-buffered 0.05% glutaraldehyde. The tissue samples were allowed to crosslink in the glutaraldehyde solution for approximately 90 hours. They were then subjected to a four-hour 2% glutaraldehyde bath for sterilization. The tissue samples were then divided into ten test and control groups packaged in 150 ml of the following solutions, shown in Table 6. All packages containing HEPES or Tris were adjusted to pH 7.4. Each group was prepared in duplicate, one for E-beam and one for control.

TABLE 6

Packaging Solutions

| Group | 0.9% Sodium Chloride | 11.0 units Catalase | 0.2 M HEPES | 0.05 M Tris |
|---|---|---|---|---|
| 1 | X | | | |
| 2 | | | X | |
| 3 | | X | X | |
| 4 | X | X | | |
| 5 | | | | X |

Each group contained approximately 13 samples of crosslinked pericardium. Samples were placed into radiation-resistant polyethylene pouches, filled with the appropriate solution, and heat sealed. Each pouch was then placed into a secondary pouch to assure against leakage. The test samples were E-beam irradiated at 2.5 Mrad and tested for $T_s$.

The use of bovine pericardium for this example allowed a much greater sample size for each test and control group. The results displayed in Table 7 suggest that the mean $T_s$ depression observed for tissue samples stored in 0.05M Tris buffer was less than any method of radioprotection attempted to date (Δ=2.5° C.); the mean $T_s$ value for these samples was 80.2° C. The experiment described in Example 13 was then designed to further evaluate the effects of Tris when used as a packaging solution for E-beam and gamma irradiated products. Results of the $T_s$ analyses:

TABLE 7

Shrink Temperature Results - Example 12

| Group Number | Mean T (° C.) | Standard Deviation | in $T_8$ due to E-beam (° C.) |
|---|---|---|---|
| 1A (saline, control) | 82.9 | 0.9 | — |
| 1B (saline, E-beam, 2.5 Mrad) | 78.7 | 0.5 | 4.2 |
| 2A (HEPES, control) | 83.3 | 0.7 | — |
| 2B (HEPES, E-beam, 2.5 Mrad) | 78.7 | 0.7 | 4.6 |
| 3A (HEPES + catalase, control) | 83.0 | 1.0 | — |
| 3B (HEPES + catalase, E-beam, 2.5 Mrad) | 78.8 | 0.6 | 4.2 |
| 4A (saline + catalase, control) | 82.9 | 0.5 | — |
| 4B (saline + catalase, E-beam, 2.5 Mrad) | 79.2 | 0.7 | 3.7 |
| 5A (tris, control) | 82.7 | 0.6 | — |
| 5B (tris, E-beam, 2.5 Mrad) | 80.2 | 1.03 | 2.5 |

Example 13. Pericardial tissue was received and crosslinked as described in Example 12 above. Based on $T_s$ results received from the tissue E-beam sterilized in Example 12, only two of the solutions were prepared for this example: 0.9% sodium chloride and 0.05M Tris. Approximately 30 samples of tissue were packaged in each of the two solutions in polyethylene pouches and gamma sterilized at a dose ranging from 3.1 to 3.4 Mrad. A duplicate set of samples was E-beam irradiated under a 10 MeV accelerator. The 10 MeV accelerator is capable of penetrating and sterilizing tissue packaged in a standard glass vial or a vial similar dimensions. The samples were E-beam irradiated at a dose ranging from 1.09 to 1.42 Mrad. The samples were then evaluated for $T_s$. Five bovine carotid artery grafts were also subjected to each process to determine if the addition of Tris to the packaging solution effects tissue damage detectable by $T_s$.

The data presented in Tables 9 and 10 below suggests that there is less of a $T_s$ depression when Tris, rather than saline, is used as the storage solution for carotid artery grafts with gamma irradiation.

There was not a significant difference in $T_s$ values obtained using gamma irradiated pericardium packaged in saline or Tris. The reason for the minimal depression observed for tissue packaged in saline cannot be explained, especially since graft tissue irradiated simultaneously in the same box exhibited a mean depression of 4.5° C. The actual dose administered to this batch of tissue ranged from 3.1–3.4 Mrad.

$T_s$ results of Example 13 E-beam and gamma sterilized bovine carotid artery are detailed in Tables 8 and 9 below:

TABLE 8

Gamma Sterilized (3.1–3.4 Mrad)
Carotid Artery Tissue - (0.05 M Tris)

| Serial No. | Solution | $T_s$ (° C.) Control | $T_s$ (° C.) Sterilized | Δ |
|---|---|---|---|---|
| 91-197-32 | Tris | 84.2 | 80.4 | 3.8 |
| 91-197-33 | Tris | 84.2 | 81.0 | 3.2 |
| 91-197-50 | saline | 84.0 | 79.8 | 4.2 |
| 91-197-86 | Tris | 84.6 | 82.2 | 2.4 |
| 91-197-92 | saline | 84.6 | 79.8 | 4.8 |
| Mean Saline | | 84.3 ±0.4 n = 2 | 79.8 ±0.0 n = 2 | 4.5 ±0.4 n = 2 |
| Mean Tris | | 84.3 ±0.2 n = 3 | 81.2 ±0.9 n = 3 | 3.1 ±0.7 n = 2 |

TABLE 9

$T_s$: E-Beam (1.25 Mrad)
Carotid Artery Tissue - (0.05 M Tris)

| Serial No. | Solution | $T_s$ (° C.) Control | $T_s$ (° C.) Sterilized | Δ |
|---|---|---|---|---|
| 91-197-53A | Saline | 83.0 | 80.0 | 3.0 |
| 91-197-53B | Saline | | 80.0 | |
| 91-197-75A | Saline | 84.6 | 83.0 | 1.6 |
| 91-197-75B | Saline | | 82.0 | |
| 91-197-41A | Tris | 84.4 | 83.0 | 1.4 |
| 91-197-41B | Tris | | N/A | |
| 91-197-72A | Tris | 84.6 | 83.0 | 1.6 |
| 91-197-72B | Tris | | 83.0 | |
| 91-197-79A | Tris | 81.4 | 83.0 | -1.6 |
| 91-197-79B | Tris | | 83.0 | |
| Mean Saline | | 83.8 ±1.1 n = 2 | 81.3 ±1.5 n = 4 | 2.3 ±1.0 n = 2 |
| Mean Tris | | 83.5 ±1.8 n = 3 | 83.0 ±0.0 n = 5 | 0.5 ±1.8 n = 3 |

$T_s$ data from E-beam and gamma irradiated bovine pericardium is summarized in Tables 10 and 11 below.

TABLE 10

$T_s$: E-Beam Sterilized (1.25 Mrad) Bovine Pericardial Tissue

| | Saline | | 0.05 M Tris | |
|---|---|---|---|---|
| | Control | Sterilized | Control | Sterilized |
| Mean | 81 | 81 | 81 | 81 |
| Std. Dev. | 2 | 1 | 1 | 1 |
| n= | 14 | 27 | 15 | 32 |
| Mean Δ after 1.25 | | 0 | | 0 |

TABLE 11

$T_s$: Gamma Sterilized (3.1–3.4 Mrad) Bovine Pericardial Tissue

| | Saline | | 0.05 M Tris | |
|---|---|---|---|---|
| | Control | Sterilized | Control | Sterilized |
| Mean | 81.4 | 78.6 | 81.7 | 79.2 |
| Std. Dev. | 2.2 | 0.9 | 1.5 | 1.1 |
| n= | 14 | 28 | 15 | 30 |
| Mean Δ after 3.1–3.4 Mrad | | 2.8 | | 2.5 |

Example 14. Approximately fifty bovine carotid artery grafts were processed under standard operating procedures, except that half of the arteries were stored in saline rather than water immediately after harvesting. Prior to fixation, the grafts were stretched 45% over their unstretched lengths. Fixation included a 24-hour exposure to 50 mM citrate-buffered 0.1% glutaraldehyde followed by 4.5 hours in citrate-buffered 2% glutaraldehyde. The glutaraldehyde was drained from the fixation tank and replaced with 20 liters of RO-purified water to remove bulk excess glutaraldehyde and allowed to sit for approximately 20 minutes. The entire volume of water was then replaced with fresh water and allowed to sit for 23 hours for further diffusion of glutaraldehyde from the graft tissue. The water was then drained and filled with two more 20-liter aliquots of water and allowed to diffuse for approximately 20 more hours. At this point the water was replaced one final time prior to packaging.

Grafts originally stored in water and grafts originally stored in saline were evenly divided among three test groups. Those test groups were identified by various storage solutions: 0.9% sodium chloride, 0.05M Tris in 0.9% sodium-chloride adjusted to pH 7.4, and 0.1M Tris adjusted to pH 7.4. The grafts were packaged in glass vials on glass mandrels and capped with the standard silicone-lined caps.

The grafts in each group were evenly divided into subgroups. One half of the grafts were exposed to gamma radiation with a dose ranging from 2.02 to 2.24 Mrad. The other half were E-beam sterilized at a dose ranging from 2.43 to 2.55 Mrad. The grafts were tested for the following characteristics: radial tensile strength, suture retention strength, and $T_s$. Tissue samples were also removed for histological evaluation using Masson Trichrome, Hematoxylin and Eosin, Verhoeff's Elastica staining. Solution samples were removed from each unit for determination of pH (before and after irradiation), osmolality, and glutaraldehyde content.

The grafts that were gamma sterilized were found to be somewhat discolored. Externally, the adventitial surfaces appeared grayish in color. A small number of grafts excised longitudinally revealed a grayish-purple lumenal aspect. No structural changes in the produce were apparent, however. Critical Surface Tension (CST) analysis was performed on six of the products (two from each of the three storage solutions) to determine whether the discoloration was caused by constitutional changes at the molecular level on the lumenal surface.

The quickest and most sensitive method of obtaining this information is by evaluating the wettability of the surfaces, which may be determined by measuring liquid drop contact angle. Molecules deeper than 5–10 Å from the surface have a negligible effect on surface/liquid interactions, so therefore, the contact angle is determined only by forces contributed by surface molecules. The contact angle is dictated by the balance of cohesive forces in the drop trying to curl it into a ball and adhesive forces between the liquid and the solid surface trying to cause the drop to spread.

CST is visualized by creating a Zisman plot, in which the cosines of contact angles of a series of pure alkanes are plotted against the surface tensions of the various liquids. A linear regression may be obtained by plotting this data. This CST is defined as the value on the surface tension axis that corresponds to cosine $\theta=1$ (or contact angle=0°) for that particular surface. Liquids that have surface tensions below the resulting CST will wet the surface and liquids with surface tensions greater than the CST will yield observable contact angles.

Contact angles were measured using a Rame-hart goniometer per Inspection Procedure 690028. The fluids used in the analysis of the biological graft material were diiodomethane, bromo-naphthalene, methyl-naphthalene, and hexadecane. CST values for the surfaces tested were obtained by plotting the cosines of the observed contact angles against the surface tensions of the four test fluids and extrapolating the resulting line to cosine $\theta=1$. The x-value at that point is defined as the CST.

Results of the CST analysis are displayed in Table 12 below:

TABLE 12

CST: Gamma-Sterilized Bovine Carotid Artery Tissue

| Sample Number | CST ($\gamma$C)(dynes/cm) |
|---|---|
| 91-295-11S | 26.4 |
| 91-295-49S | 26.8 |
| 91-295-97T | 26.6 |
| 91-295-44T | 26.4 |
| 91-295-58ST | 27.1 |
| 91-295-81ST | 25.7 |
| Mean | 26.5 |
| Standard Deviation | 0.5 |

CST testing on both glutaraldehyde crosslinked bovine carotid artery and median artery tissue in the past has consistently yielded results in the range of 24–30 dynes/cm. The data above suggests no differences from non-irradiated tissue processed similarly in the past, as all $\gamma$C values lie well within the normal historical range. The use of CST to predict blood/surface interactions regarding thrombogenicity is not possible as there exists many mechanical and biological factors outside the realm of interfacial chemistry that significantly effect thrombotic activity. The test method was used only to detect deviations in surface molecular composition after irradiation from typical graft tissue.

Results of $T_s$ testing performed on E-beam and gamma sterilized carotid artery graft tissue from Example 14 are summarized in Tables 13 and 14 below.

TABLE 13

$T_s$ of E-Beam Sterilized (2.43–2.55 Mrad Carotid Artery Product

| | $T_s$ (° C.) | | | | | |
|---|---|---|---|---|---|---|
| | Saline | | 0.1 M Tris | | Saline/0.05 M Tris | |
| | Control | E-Beam | Control | E-Beam | Control | E-Beam |
| Mean | 83 | 79 | 83 | 80 | 82 | 80 |
| Std. Dev. | 1 | 2 | 1 | 1 | 1 | 1 |
| n= | 5 | 5 | 5 | 10 | 5 | 9 |
| Mean Δ after 2.43–2.55 Mrad | | 4 | | 3 | | 2 |

TABLE 14

$T_s$ of Gamma Sterilized (2.02–2.24 Mrad) Carotid Artery Product

| | $T_s$ (° C.) | | | | | |
|---|---|---|---|---|---|---|
| | Saline | | 0.1 M Tris | | Saline/0.05 M Tris | |
| | Control | Gamma | Control | Gamma | Control | Gamma |
| Mean | 83 | 80 | 83 | 81 | 82 | 81 |
| Std. Dev. | 1 | 1 | 1 | 1 | 1 | 1 |
| n= | 5 | 4 | 5 | 9 | 4 | 8 |
| Mean Δ after 2.02–2.24 Mrad | | 3 | | 2 | | 1 | pH of storage solutions before and after irradiation was tested and those results are summarized in Table 15 below. (Determination of pH prior to irradiation was performed on stock solutions rather than for individual graft units. Therefore, n=1 for all pre-sterilization samples).

TABLE 15 pH of Storage Solutions Pre- and Post-Irradiation*

| | E-Beam (2.43–2.55 Mrad) | | Gamma (2.0–2.24 Mrad) | |
|---|---|---|---|---|
| Solution | Pre | Post | Pre | Post |
| Saline | 5.95 | 6.52 ± 0.11 n = 6 | 5.95 | 6.35 ± 0.05 n = 4 |
| 0.1 M Tris | 7.40 | 7.18 ± 0.03 n = 10 | 7.40 | 7.27 ± 0.05 n = 10 |
| Saline/ 0.05 M Tris | 7.40 | 6.98 ± 0.07 n = 10 | 7.40 | 7.06 ± 0.06 n = 10 |

*pH values for solutions containing Tris may be somewhat inaccurate as it has since been discovered that a special glass calomel electrode is required for measuring Tris.

Results of physical tests performed on E-beam sterilized product from Example 14 is summarized in Table 16 below.

TABLE 16

Physical Testing Results - E-beam Sterilized Product (2.43–2.55 Mrad)

|  | Saline | 0.1 M Tris | 0.05 M Tris/Saline |
|---|---|---|---|
| Wall Thickness (mm) | | | |
| Mean | 0.94 | 1.11 | 0.99 |
| Std. Dev. | 0.18 | 0.04 | 0.17 |
| n= | 108 | 189 | 171 |
| Radial Tensile Strength (lbs) | | | |
| Mean | 4.29 | 4.19 | 4.77 |
| Std. Dev. | 1.22 | 0.90 | 1.12 |
| n= | 18 | 30 | 30 |
| Suture Retention Strength (lbs) | | | |
| Mean | 2.18 | 2.14 | 2.05 |
| Std. Dev. | 0.55 | 0.87 | 0.52 |
| n= | 18 | 36 | 27 |

Results of physical tests performed on gamma sterilized product from Example 14 summarized in Table 17 below.

TABLE 17

Physical Testing Results - Gamma Sterilized Product (2.02–2.24 Mrad)

|  | Saline | 0.1 M Tris | 0.05 M Tris/Saline |
|---|---|---|---|
| Wall Thickness (mm) | | | |
| Mean | 0.94 | 1.00 | 0.99 |
| Std. Dev. | 0.25 | 0.18 | 0.17 |
| n= | 72 | 162 | 197 |
| Radial Tensile Strength (lbs) | | | |
| Mean | 4.32 | 4.45 | 4.39 |
| Std. Dev. | 0.72 | 0.88 | 1.72 |
| n= | 12 | 27 | 33 |
| Suture Retention Strength (lbs) | | | |
| Mean | 1.83 | 1.91 | 2.02 |
| Std. Dev. | 0.43 | 0.72 | 0.57 |
| n= | 12 | 27 | 33 |

Osmolality of solutions samples post-E-beam are summarized in Table 18 below.

TABLE 18

Post-E-Beam (2.43–2.55 Mrad) Packaging Solution Osmolality (osmolality expressed in mOsm/L)

|  | Saline | 0.1 M Tris | Saline/0.05 M Tris |
|---|---|---|---|
| Mean | 278 | 156 | 344 |
| Std. Dev. | 19 | 5 | 9 |
| n = | 3 | 8 | 8 |

Residual glutaraldehyde levels are summarized in Table 19 below.

TABLE 19

Residual Glutaraldehyde Levels

Residual Glutaraldehyde (ppm)

| | E-Beam (2.43–2.55 Mrad) | | | Gamma (2.02–2.24 Mrad) | | |
|---|---|---|---|---|---|---|
| | Saline | 0.05 M Tris | Saline/ 0.1 M Tris | Saline | 0.05 M Tris | Saline/ 0.1 M Tris |
| Mean | 0.00 | 14.18 | 7.95 | 1.00 | 10.39 | 7.38 |
| Std. Dev. | N/A | 2.73 | 2.00 | 0.37 | 2.38 | 1.93 |
| n= | 12 | 20 | 20 | 4 | 10 | 10 |

Results (Example 14):
1. Results of CST testing suggest there were no conformational deviations on the lumenal surfaces of the irradiated products that were accountable for the noted discoloration.
2. $T_s$ data for E-beam sterilized carotid artery product suggest that the least amount of change resulted from packaging the tissue in the saline/0.05M Tris solution, followed by 0.1M Tris and saline. The same trend was noted for gamma sterilized product. The mean $T_s$ of the E-beam sterilized product was approximately 2° C. less than the control material, while the $T_s$ for the gamma sterilized product was approximately 1° C. lower than the control.
3. Physical test results (radial tensile, suture retention, and wall thickness) of E-beam and gamma sterilized graft product appear to be comparable to the current product, with and without the use of Tris as a packaging solution additive.
4. Of the two buffered storage solutions used in this example, the 0.1M Tris appeared to have the greater buffering capacity: a decrease of 0.22 pH units compared to 0.42 with the saline/0.05M Tris combination following exposure to E-beam, and a decrease of 0.13 for 0.1M Tris compared to 0.34 for saline/0.05M Tris following gamma radiation. Based upon the superior buffering capacity of the more concentrated buffer, a saline/0.1M Tris storage solution was implemented in Example 15. It was discovered after these measurements were determined that a glass calomel electrode was necessary for testing pH of solutions containing Tris. The values, therefore, may be inaccurate.
5. The osmolality of the storage solutions was analyzed to gain some understanding of the tonicity of the various solutions used in these studies. It is advisable to maintain a near-physiological osmolality to prevent excessive swelling or shrinking of cellular components in the graft wall which may contribute to stress on the collagen matrix. The final concentration of solute in the packaging solution may be adjusted to approach physiological values.
6. Residual glutaraldehyde analysis revealed a significant increase in concentration of glutaraldehyde, or another compound with the identical retention time under HPLC, following both E-beam and gamma radiation. The identity or origin of the peak has not yet been determined.

Example 15. Thirty bovine carotid artery grafts were placed on glass mandrels and stretched to 120% of their incoming lengths (stretch ratio method) and placed in a 50mM citrate buffered 0.1% glutaraldehyde solution for a period of 24 hours. The grafts were then pre-sterilized in a 50mM citrate buffered 2% glutaraldehyde solution for approximately 4 hours. Following sterilization, the grafts were rinsed with water: three fixation tank volumes over a period of four days.

The grafts were packaged in glass vials in one of two packaging solutions: saline or 0.1M Tris brought up in saline. The pH of the saline/Tris solution was adjusted to 7.4 prior to packaging.

The test groups were divided into two groups. One group was exposed to gamma radiation with a dose ranging from 2.5–2.6 Mrad. The other half was E-beam sterilized at a dose of 2.6 Mrad. The irradiated grafts were evaluated as follows: radial tensile strength, suture retention strength, and $T_s$. Solution samples were removed from each unit for determination of pH (before and after irradiation), osmolality, and glutaraldehyde content.

Results of $T_s$ for Example 15 E-beam sterilized product are summarized in Table 20 below.

TABLE 20

$T_s$ of E-Beam Sterilized (2.6 Mrad) Carotid Artery Product

| | $T_s$ (° C.) | | | |
|---|---|---|---|---|
| | Saline | | Saline/0.1 M Tris | |
| | Control | E-Beam | Control | E-Beam |
| Mean | 84 | 78 | 83 | 79 |
| Std. Dev. | 1 | 1 | 1 | 1 |
| n= | 6 | 6 | 6 | 6 |
| Mean Δ 2.6 Mrad | | 6 | | 4 |

Results of $T_s$ for Example 15 gamma sterilized product is summarized in Table 21 below.

TABLE 21

$T_s$ of Gamma Sterilized (2.5–2.6 Mrad) Carotid Artery Product

| | $T_s$ (° C.) | | | |
|---|---|---|---|---|
| | Saline | | Saline/0.1 M Tris | |
| | Control | Gamma | Control | Gamma |
| Mean | 84 | 80 | 83 | 81 |
| Std. Dev. | 1 | 0.4 | 1 | 1 |
| n= | 6 | 6 | 6 | 6 |
| Mean Δ after 2.6 Mrad | | 4 | | 2 |

Results of physical tests performed on gamma sterilized product from Example 15 are summarized in Table 22 below.

TABLE 22

Physical Testing Results - Gamma Sterilized Product (2.5–2.6 Mrad)

| | Saline | 0.1 M Tris/Saline |
|---|---|---|
| Wall Thickness (mm) | | |
| Mean | 1.04 | 1.03 |
| Std. Dev. | 0.20 | 0.19 |
| n= | 108 | 108 |
| Radial Tensile Strength (lbs) | | |
| Mean | 4.32 | 3.67 |
| Std. Dev. | 1.22 | 1.03 |
| n= | 18 | 18 |
| Suture Retention Strength (lbs) | | |
| Mean | 2.31 | 2.13 |
| Std. Dev. | 0.89 | 0.64 |
| n= | 18 | 18 |

Results of physical tests performed on E-beam sterilized product from Example 15 are summarized in Table 23 below:

TABLE 23

Physical Testing Results - E-Beam Sterilized Product (2.6 Mrad)

| | Saline | 0.1 M Tris/Saline |
|---|---|---|
| Wall Thickness (mm) | | |
| Mean | 1.01 | 0.95 |
| Std. Dev. | 0.20 | 0.18 |
| n= | 108 | 108 |
| Radial Tensile Strength (lbs) | | |
| Mean | 4.49 | 3.99 |
| Std. Dev. | 0.84 | 0.99 |
| n= | 18 | 18 |
| Suture Retention Strength (lbs) | | |
| Mean | 2.44 | 2.20 |
| Std. Dev. | 0.68 | 0.66 |
| n= | 18 | 18 |

Residual glutaraldehyde results are detailed in Table 24 below.

TABLE 24

Residual Glutaraldehyde Levels

Residual Glutaraldehyde Levels

| E-Beam (2.6 Mrad) | | Gamma (2.5–2.6 Mrad) | |
|---|---|---|---|
| Saline | Saline/Tris | Saline | Saline/Tris |
| 2.25 | 9.83 | 0.43 | 10.19 |
| 1.82 | 9.60 | 0.54 | 13.52 |
| 1.69 | 10.94 | 0.42 | 8.96 |
| 1.69 | 10.90 | 0.74 | 13.70 |
| 1.83 | 9.50 | 0.27 | 12.71 |
| 1.91 | 10.13 | | |
| 0.00 | 12.65 | | |
| 0.00 | 12.16 | | |
| 1.46 | 7.94 | | |
| 1.48 | 8.19 | | |
| 2.04 | 8.49 | | |
| 2.46 | 8.53 | | |
| Mean: 1.55 | 9.91 | 0.48 | 11.82 |
| Std. Dev.: 0.78 | 1.53 | 0.17 | 2.12 |

Results:
1. $T_s$ results of both gamma and E-beam sterilized product appear to be equivalent regardless of packaging solution, saline or Tris/saline.
2. Wall thickness values were comparable for all test groups.
3. Radial tensile strength of tissue stored in saline was somewhat greater for both methods of irradiation: 13% greater for E-beam and 18% greater for gamma. Tensile strength results of product stored in saline were slightly higher for product sterilized with E-beam: 4.49 lbs for E-beam and 4.32 lbs for gamma.
4. Similarly, suture retention strength of tissue stored in saline was greater for both methods of irradiation: 11% greater for E-beam and 8% greater for gamma. Suture retention results of product stored in saline were slightly higher for product sterilized with E-beam: 22.4 lbs for E-beam and 2.31 lbs for gamma.
5. As in Example 14, residual glutaraldehyde analysis revealed a significant increase in concentration of a compound with the identical retention time as glutaraldehyde under HPLC, following both E-beam and gamma radiation.

Example 16. Microbiological Considerations. A study was performed involving the E-beam sterilization of median artery tissue inoculated with *Bacillus pumilus* (0.5–5.0–$10^6$ spores per package). Ten samples were irradiated at 2.5 Mrad. There was no bacterial colonization present from any of the ten test samples after a fourteen day incubation period. When test results suggested a decrease in $T_s$ after a dose of 2.5 Mrad, a follow-up study was performed to determine the lowest dose that would result in negative sterility testing with *B. pumilus*. Dose rates of 0.6 and 1.25 were applied to tissue inoculated with *B. pumilus* as described above. The samples irradiated at 1.25 Mrad exhibited a 100% kill rate while the mean $T_s$ of group (n=5) was 80.2° C.

Example 17. The example determines the effectiveness of electron beam sterilization on biological graft tissue inoculated with a radiation-resistant organism.

Twenty-eight bovine median arteries were prepared SOP (stripped, ficin digested, and glutaraldehyde crosslinked). Grafts were aseptically packaged in glass vials in sterile saline and allowed to remain on the shelf for a period of 14 days to allow diffusion of excess glutaraldehyde from the tissue.

Twelve grafts were removed from their respective vials and placed into a container with 7 liters of sterile saline (583 ml per unit) and allowed to soak for a period of 60 minutes to further diffuse residual glutaraldehyde. Each graft was placed into a foil laminate E-beam sterilization pouch. Into each pouch, 150 ml sterile saline was added and each was inoculated with the following:

0.1 ml of *Bacillus pumilus*

0.5 to $5.0 \times 10^6$ spores/0.1 ml (organism indicated for radiation)

Upon completion of the packaging process, one pouch was omitted from the group intended for E-beam exposure to serve as a positive control. Test samples were then sterilized using E-beam radiation.

Ten out of ten test samples exhibited no bacterial colonization after a fourteen day incubation period. The positive control sample exhibited bacterial colonization. Electron beam sterilization was effective in sterilizing 100% (10/10) of bovine-derived biological graft products packaged in saline and inoculated with a known radiation-resistant organism.

Example 18. This example tests the effects of electron beam sterilization on the physical properties of biological graft material. The following parameters were evaluated:

Radial Tensile Strength
Suture Retention
Leak Rate
Bursting Strength
Shrink Temperature
Critical Surface Tension
Histological Sectioning Twenty-eight bovine median arteries were stripped, tied, sutured, digested, and glutaraldehyde fixed. The grafts were subjected to standard glutaraldehyde reduction steps to reduce glutaraldehyde residuals. Grafts were packaged in 150 ml sterile saline in polyethylene pouches and heat sealed. Sterility and LAL samples were taken at the repacking step to assure that product being submitted for testing was sterile at the time of packaging. Samples were then exposed to E-beam radiation to sterilize the packaged arteries.

Results of physical testing is displayed in Table 25 below.

TABLE 25

| Test | E-Beam (mean, std) | Control (mean, std) |
|---|---|---|
| Radial Tensile (lbs) | 2.52 | 3.12 |
| | 1.23 | 0.82 |
| Suture Retention (lbs) | 0.88 | 1.19 |
| | 0.37 | 0.38 |
| Wall Thickness (mm) | 0.94 | 1.03 |
| | 0.18 | 0.24 |
| Leak Test (ml/minute) | 2.0 | 2.3 |
| | 1.4 | 4.5 |
| Bursting Strength (psi) | 50.0 | 61.0 |
| | 19.3 | 21.7 |
| Shrink Temperature (° C.) | 77.4 | 83.4 |
| | 0.2 | 1.1 |
| Critical Surface Tension (γC, dynes/cm) | 27.2 | 26.5 |
| | 0.8 | 1.3 |

While the invention has been described in some detail by way of illustration and example, it should be understood that the invention is susceptible to various modifications and alternative forms, and is not restricted to the specific embodiments set forth. It should be understood that these specific embodiments are not intended to limit the invention but on the contrary, the intention is to cover all modifications, equivalents, and alternatives falling within the spirit and scope of the invention.

What is claimed is:

1. A sterilized collagen-containing biological tissue suitable for implantation comprising a crosslinked, hydrated collagen-containing tissue irradiated with a beam of accelerated electrons.

2. The tissue of claim 1 wherein said crosslinked tissue has been crosslinked by glutaraldehyde.

3. A packaged sterilized collagen-containing biological tissue suitable for implantation comprising a crosslinked, hydrated collagen-containing biological tissue sealed in a container and exposed to electron-beam radiation.

4. A collagen-containing biological tissue suitable for implantation wherein said biological tissue comprises tissue irradiated with a beam of accelerated electrons, and wherein said biological tissue has at least one improved performance characteristic relative to a tissue not irradiated with accelerated electrons, and wherein said improved performance characteristic is selected from the group consisting of greater softness, greater kink resistance, improved suturability, greater tensile strength, no loss of tensile strength, increased effective orifice area, decreased pressure gradients, and enhanced durability.

5. The tissue of claim 1 wherein said tissue has been irradiated at a dose rate of approximately 7800 grays per minute.

6. The tissue of claim 3 wherein said tissue has been irradiated at a dose rate of approximately 7800 grays per minute.

7. The tissue of claim 1 wherein said irradiated biological tissue is not significantly degraded.

8. The tissue of claim 1 further comprising an anticalcification agent.

9. The tissue of claim 1 further comprising a radioprotectant.

10. The tissue of claim 1 wherein said biological, tissue comprises a heart valve, aortic root, heart valve leaflet, vascular prosthesis or pericardial tissue.

11. The packaged tissue of claim 3 wherein the irradiated biological tissue is not significantly degraded.

12. The packaged tissue of claim 3 further comprising an anticalcification agent.

13. The packaged tissue of claim 3 further comprising a radioprotectant.

14. The packaged tissue of claim 3 wherein said biological tissue comprises a heart valve, aortic root, heart valve leaflet, vascular prosthesis or pericardial tissue.

15. The tissue of claim 4 wherein said biological tissue comprises a heart valve, aortic root, heart valve leaflet, vascular prosthesis or pericardial tissue.

16. The tissue of claim 4 wherein said improved performance characteristic is greater softness.

17. The tissue of claim 4 wherein said improved performance characteristic is greater tensile strength.

18. The tissue of claim 4 wherein said improved performance characteristic is enhanced durability.

19. The tissue of claim 4 wherein said biological tissue has a plurality of improved performance characteristic comprising greater softness, greater tensile strength and enhanced durability.

* * * * *